US007205434B2

(12) United States Patent
Hannam et al.

(10) Patent No.: US 7,205,434 B2
(45) Date of Patent: Apr. 17, 2007

(54) SULPHONAMIDES FOR CONTROL OF BETA-AMYLOID PRODUCTION

(75) Inventors: Joanne Clare Hannam, Bishops Stortford (GB); Timothy Harrison, Great Dunmow (GB); Andrew Madin, Sawbridgeworth (GB); Timothy Jason Sparey, London (GB)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 427 days.

(21) Appl. No.: 10/484,290

(22) PCT Filed: Jul. 31, 2002

(86) PCT No.: PCT/GB02/03559

§ 371 (c)(1),
(2), (4) Date: Jan. 20, 2004

(87) PCT Pub. No.: WO03/013506

PCT Pub. Date: Feb. 20, 2003

(65) Prior Publication Data

US 2004/0186147 A1 Sep. 23, 2004

(30) Foreign Application Priority Data

Aug. 6, 2001 (GB) ................................ 0119152.7

(51) Int. Cl.
*C07C 303/00* (2006.01)
*A61K 31/18* (2006.01)

(52) U.S. Cl. ............................ 564/80; 564/84; 564/86; 514/601; 514/602; 514/603

(58) Field of Classification Search ..................... None
See application file for complete search history.

(56) References Cited

U.S. PATENT DOCUMENTS 3,836,670 A 9/1974 Freed et al.

FOREIGN PATENT DOCUMENTS

WO WO 01/70677 9/2001

OTHER PUBLICATIONS

G. M. Rishton et al., "Fenchylamine Sulfonamide Inhibitors of Amyloid Beta Peptide Production by the Gamma-Secretase Proteolytic Pathway: Potential Small-Molecule Therapeutic Agents for the Treatment of Alzheimer's Disease", J. Med. Chem., vol. 43, pp. 2297-2299 (2000).

K. Wiesner et al., "Synthesis and Rearrangement Control of Substituted Benzobicycloheptane Aziridines", Can. J. Chem., vol. 51, pp. 1448-1457 (1973).

K. Wiesner et al., "Synthesis in the Series of Diterpene Alkaloids V. An Approach to Songorine", Tetrahedron Letters, No. 14, pp. 1467-1470 (1966).

*Primary Examiner*—Sikarl A. Witherspoon
(74) *Attorney, Agent, or Firm*—John C. Todaro; Melvin Winokur

(57) ABSTRACT

There is disclosed a novel class of sulphonamido-substituted bridged bicycloalkyl derivatives comprising a substitute on the bridgehead position. The compounds modulate the production of the β-amyloid precursor protein, and hence are useful in the treatment of Alzheimer's Disease.

8 Claims, No Drawings

SULPHONAMIDES FOR CONTROL OF BETA-AMYLOID PRODUCTION

CROSS REFERENCE TO RELATED APPLICATIONS

This application is a U.S. National Phase application under 35 U.S.C. § 371 of PCT Application No. PCT/GB02/03559, filed Jul. 31, 2002, which claims priority under 35 U.S.C. § 119 from GB Application No. 0119152.7, filed Aug. 6, 2001.

The present invention relates to a novel class of compounds their salts, pharmaceutical compositions comprising them, processes for making them and their use in therapy of the human body. In particular, the invention relates to compounds which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ), and although the exact role of the plaques in the onset and progress of AD is not fully understood, it is generally accepted that suppressing or attenuating the secretion of Aβ is a likely means of alleviating or preventing the condition. (See, for example, ID *research alert* 1996 1(2): 1–7; ID *research alert* 1997 2(1):1–8; Current Opinion in CPNS Investigational Drugs 1999 1(3):327–332; and Chemistry in Britain, January 2000, 28–31.)

Aβ is a peptide comprising 39–43 amino acid residues, formed by proteolysis of the much larger amyloid precursor protein. The amyloid precursor protein (APP or AβPP) has a receptor-like structure with a large ectodomain, a membrane spanning region and a short cytoplasmic tail. Different isoforms of APP result from the alternative splicing of three exons in a single gene and have 695, 751 and 770 amino acids respectively.

The Aβ domain encompasses parts of both extra-cellular and transmembrane domains of APP, thus its release implies the existence of two distinct proteolytic events to generate its $NH_2$— and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβ domain (between residues $Lys^{16}$ and $Leu^{17}$) to release α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo autocleavage.

There are relatively few reports in the literature of compounds with inhibitory activity towards β- or γ-secretase, as measured in cell-based assays. These are reviewed in the articles referenced above. Many of the relevant compounds are peptides or peptide derivatives.

A group of fenchylamine sulphonamides are disclosed as γ-secretase inhibitors in *J. Med. Chem.,* 43, 2297–9, 2000.

U.S. Pat. No. 3,836,670 discloses the N-tosyl derivatives of two benzo-fused bridged bicycloalkylamines comprising a bridgehead substituent. The compounds are disclosed as synthetic intermediates, with no indication of any pharmacological properties.

The present invention provides a novel class of non-peptidic compounds which are useful in the treatment or prevention of AD by modulating the processing of APP by the putative γ-secretase, thus arresting the production of Aβ.

The present invention provides a pharmaceutical composition comprising, in a pharmaceutically-acceptable carrier, a therapeutically effective amount of one or more compounds of formula I:

I

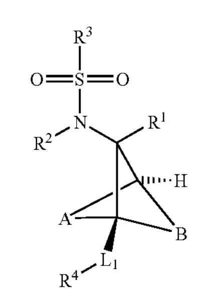

wherein:

A and B together with the carbon atoms bonded to $-L_1R^4$ and H complete a ring containing 5–10 carbon atoms, said ring bearing 0–2 substituents (in addition to $-L_1-R^4$) selected from:

=O, =S, =N—$OR^{11}$, =$CHR^{11}$, halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

and said ring optionally having fused thereto a further ring selected from $C_{6-10}$aryl, heteroaryl, heterocyclyl and $C_{5-10}$cycloalkyl, said further ring bearing 0–3 substituents independently selected from:

halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^1$ represents H, $C_{1-4}$alkyl or $C_{2-4}$alkenyl;

$R^2$ represents H, or $C_{2-6}$acyl which optionally bears a carboxylic acid or amino substituent;

$R^3$ represents $C_{1-10}$alkyl, $C_{3-10}$cycloalkyl, $C_{2-6}$alkenyl, $C_{2-6}$alkynyl, $C_{6-10}$aryl$C_{1-6}$alkyl, heteroaryl$C_{1-6}$alkyl, $C_{6-10}$aryl$C_{2-6}$alkenyl, heteroaryl$C_{2-6}$alkenyl, $C_{6-10}$aryl, heteroaryl, or heterocyclyl; wherein the alkyl, cycloalkyl, alkenyl and alkynyl groups represented by $R^3$ or forming part of a group represented by $R^3$ optionally bear a substituent selected from halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$NR^7CO_2R^8$ and —$NR^7SO_2R^8$; and the aryl, heteroaryl and heterocyclic groups represented by $R^3$ or forming part of a group represented by $R^3$ optionally bear up to 3 substituents independently selected from $R^8$, halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$NR^7CO_2R^8$ and —$NR^7SO_2R^8$;

$R^4$ represents H, halogen, Ar, heterocyclyl, CN, —$OR^9$, —$N(R^9)_2$, —$N(R^9)COR^{10}$, —$N(R^9)CO_2R^{10}$, —$OCOR^{10}$, —$COR^9$, —$C(=NOR^{11})R^9$, —$CO_2R^9$, —$OCO_2R^{10}$, —$OSO_2R^9$, —$OSO_2N(R^9)_2$, —$CON(R^9)_2$, —$OCON(R^9)_2$, or —$CSN(R^9)_2$;

$L_1$ represents a covalent bond, $C_{1-6}$alkylene, $C_{2-6}$alkenylene, $C_{2-6}$alkynylene or $C_{1-4}$alkylene-W—$C_{1-4}$alkylene where W represents O, S, $SO_2$, NH, NH—CO—NH, O—CO—O, O—CO—NH or NH—CO—O , any of the alkylene groups optionally being substituted by halogen, CN, hydroxyl or $C_{1-4}$alkoxy; provided that if $R^4$ represents H, then $L_1$ does not represent a covalent bond;

$R^7$ represents H or $R^8$; or two $R^7$ groups together with a nitrogen atom to which they are mutually attached may complete a pyrrolidine, piperidine, piperazine or morpholine ring;

$R^8$ represents $C_{1-6}$alkyl, perfluoro$C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, Ar or —$C_{1-6}$alkylAr;

$R^9$ represents H or $R^{10}$; or two $R^9$ groups together with a nitrogen atom to which they are mutually attached may complete a 3–7 membered ring comprising up to 2 heteroatoms independently selected from N, O and S in addition to the nitrogen to which the $R^9$ groups are attached, said ring being optionally substituted by up to 3 substituents independently selected from halogen, oxo, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^{10}$ represents $C_{1-6}$alkyl, perfluoro$C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, $C_{6-10}$aryl, heteroaryl, heterocyclyl, $C_{6-10}$aryl$C_{1-6}$alkyl, heteroaryl$C_{1-6}$alkyl, $C_{6-10}$aryl$C_{2-6}$alkenyl or heteroaryl$C_{2-6}$alkenyl, wherein the alkyl, cycloalkyl, alkenyl and alkynyl groups optionally bear one substituent selected from halogen, $CF_3$, $NO_2$, CN, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$; and the aryl, heteroaryl and heterocyclic groups optionally bear up to 3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^{11}$ represents H or $R^{12}$;

$R^{12}$ represents $C_{1-6}$alkyl, hydroxy$C_{1-6}$alkyl, perfluoro $C_{1-6}$alkyl, $C_{2-6}$alkenyl, $C_{2-6}$alkynyl, Ar or —$C_{1-6}$alkylAr;

Ar is phenyl or heteroaryl either of which optionally bears up to 3 substituents independently selected from halogen, OH, $CF_3$, $NO_2$, CN, $C_{1-6}$alkyl and $C_{1-6}$alkoxy;

"heterocyclyl" at every occurrence thereof means a cyclic or polycyclic system of up to 10 ring atoms selected from C, N, O and S, wherein none of the constituent rings is aromatic and wherein at least one ring atom is other than C; and "heteroaryl" at every occurrence thereof means a cyclic or polycyclic system of up to 10 ring atoms selected from C, N, O and S, wherein at least one of the constituent rings is aromatic and wherein at least one ring atom of said aromatic ring is other than C;

or a pharmaceutically acceptable salt thereof.

In a second aspect, the invention provides a compound of formula I as defined above, or a pharmaceutically acceptable salt thereof, with the proviso that:

if A represents 1,2-benzenediyl, and B represents —$CH_2CH_2CH_2$—, and $R^1$ and $R^2$ each represents H, and $R^3$ represents 4-methylphenyl, and $L_1$ represents —$CH_2$—;

then $R^4$ does not represent H or p-toluenesulfonyloxy.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Groups comprising up to 6 carbon atoms are preferred. Particular alkyl groups include methyl, ethyl, n-propyl, isopropyl and t-butyl. Derived expressions such as "$C_{2-6}$alkenyl", "hydroxy$C_{1-6}$alkyl", "heteroaryl" $C_{1-6}$alkyl, "$C_{2-6}$alkynyl" and "$C_{1-6}$alkoxy" are to be construed in an analogous manner.

The expression "perfluoro$C_{1-6}$alkyl" as used herein refers to alkyl groups as defined above comprising at least one —$CF_2$— or —$CF_3$ group.

The expression "$C_{3-10}$cycloalkyl" as used herein refers to nonaromatic monocyclic or fused bicyclic hydrocarbon ring systems comprising from 3 to 10 ring atoms. Examples include cyclopropyl, cyclobutyl, cyclopentyl, cyclohexyl, cyclohexenyl and decalinyl. Groups comprising up to 6 carbon atoms are preferred.

The expression "$C_{3-6}$cycloalkyl($C_{1-6}$)alkyl" as used herein includes cyclopropylmethyl, cyclobutylmethyl, cyclopentylmethyl and cyclohexylmethyl.

The expression "$C_{2-6}$acyl" as used herein refers to ($C_{1-5}$ alkyl)carbonyl groups, such as acetyl, propanoyl and butanoyl, including cycloalkyl derivatives such as cyclopentanecarbonyl and cyclobutanecarbonyl.

$C_{6-10}$aryl groups include phenyl and naphthyl, preferably phenyl.

The expression "$C_{6-10}$aryl$C_{1-6}$alkyl," as used herein includes benzyl, phenylethyl, phenylpropyl and naphthylmethyl. Benzyl is a preferred example.

The expression "heterocyclyl" as used herein means a cyclic or polycyclic system of up to 10 ring atoms selected from C, N, O and S, wherein none of the constituent rings is aromatic and wherein at least one ring atom is other than carbon. Preferably not more than 3 ring atoms are other than carbon. Suitable heterocyclyl groups include azetidinyl, pyrrolidinyl, terahydroflryl, piperidinyl, piperazinyl, morpholinyl, thiomorpholinyl, 2,5-diazabicyclo[2.2.1]heptyl and 2-aza-5-oxabicyclo[2.2.1]heptyl. Groups comprising up to 6 ring atoms are preferred.

The expression "heteroaryl" as used herein means a cyclic or polycyclic system of up to 10 ring atoms selected from C, N, O and S, wherein at least one of the constituent rings is aromatic and wherein at least one ring atom is other than carbon. Preferably not more than 3 ring atoms are other than carbon. Where a heteroaryl ring comprises two or more atoms which are not carbon, not more than one of said atoms may be other than nitrogen. Examples of heteroaryl groups include pyridinyl, pyridazinyl, pyrimidinyl, pyrazinyl, pyrrolyl, furyl, thienyl, pyrazolyl, oxazolyl, isoxazolyl, thiazolyl, isothiazolyl, imidazolyl, oxadiazolyl, triazolyl and thiadiazolyl groups and benzo-fused analogues thereof. Further examples of suitable heteroaryl ring systems include 1,2,4-triazine, 1,3,5-triazine, 1,2,3,4-tetrahydroisoquinoline, imidazo[2,1-b]thiazole and benzo[1,4]dioxin. Groups comprising 5 or 6 ring atoms are preferred.

The term "halogen" as used herein includes fluorine, chlorine, bromine and iodine, of which fluorine and chlorine are preferred. For use in medicine, the compounds of formula I may advantageously be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Regardless of the presence or absence of asymmetric centres, the compounds in accordance with the invention generally exist as enantiomers by virtue of the asymmetry of the molecule as a whole, their interconversion being prevented by the rigidity of the bridged bicycloalkyl ring structure. It is to be understood that all such isomers and mixtures thereof in any proportion are encompassed within the scope of the present invention, and that structural formulae depicting asymmetric molecules of this type shall be representative of both of the possible enantiomers, unless otherwise indicated.

The compounds of formula I are sulphonamido-substituted bridged bicycloalkyl derivatives, optionally comprising a further fused ring system, and comprising a bridgehead substituent represented by -$L_1R^4$.

In formula I, A and B together with the carbon atoms bonded to -$L_1R^4$ and H (the bridgehead carbons) complete a ring of 5–10 carbon atoms, said ring optionally bearing 0–2 substituents as defined previously, and said ring optionally having fused thereto a further ring selected from $C_{6-10}$aryl, heteroaryl, heterocyclyl and $C_{5-10}$cycloalkyl which may also be substituted as defined previously. Preferably, the ring completed by A and B contains 6–9 carbon atoms, most preferably 7 or 8 carbon atoms. If a fused ring is present, it is preferably fused to A, and is preferably selected from $C_{6-10}$aryl and heteroaryl, with benzene most preferred.

In a subset of the compounds of formula I,

A is selected from —$(CXY)_p$—; —$(CXY)_q$CY═CY$(CXY)_r$—; and

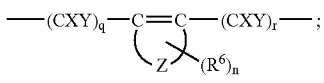

and B is —$(CXY)_p$— or —$(CXY)_q$CY═CY$(CXY)_r$—;

where X is selected from H, halogen, $NO_2$, CN, $R^{12}$, —$OR^{11}$, —$SR^{11}$, —$SO_2R^{12}$, —$COR^{11}$, —$CO_2R^{11}$, —CON$(R^{11})_2$, —$OCOR^{12}$, —$N(R^{11})_2$ and —$NR^{11}COR^{12}$;

Y is H or $C_{1-6}$alkyl;

or X and Y together represent ═O, ═S, ═N—$OR^{11}$ or ═$CHR^{11}$;

with the proviso that neither A nor B comprises more than one —(CXY)— moiety that is other than —$CH_2$—;

Z completes an aryl or heteroaryl ring;

$R^6$ represents halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

n is 0, 1 or 2;

p is 2, 3 or 4; and q and r are independently 0 or 1.

Preferred values of n are 0 and 1.

Preferred values of p are 2 and 3.

q and r are preferably both 1.

X and Y are preferably both H, or together represent ═O, ═NOH or ═$CH_2$.

Z preferably completes a benzene ring.

$R^6$ (if present) is preferably halogen, CN, Ar, —$OR^{11}$ or —$N(R^{11})_2$.

Examples of structures completed by A and B include, but are not restricted to:

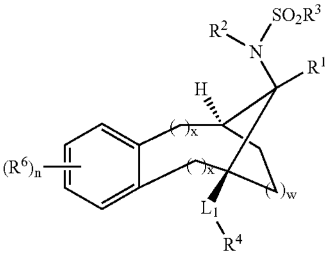
;
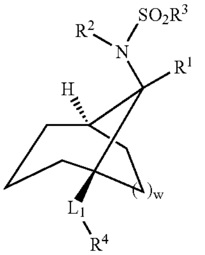
;
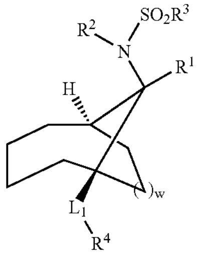
; and
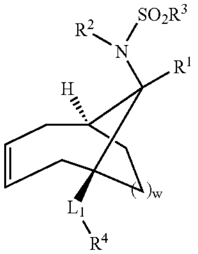

where w is 1 or 2 and each x is independently 0 or 1. Preferably at least one x is 1.

$R^1$ represents H, $C_{1-4}$alkyl (such as methyl, ethyl or propyl) or $C_{2-6}$alkenyl (such as allyl). $R^1$ is preferably H or methyl, and most preferably is H.

$R^2$ represents H or $C_{2-6}$acyl which optionally bears a carboxylic acid or amino substituent. $R^2$ preferably represents H.

$R^3$ represents $C_{1-10}$alkyl, $C_{3-10}$cycloalkyl, $C_{2-6}$alkenyl, $C_{2-6}$alkynyl, $C_{6-10}$aryl$C_{1-6}$alkyl, heteroaryl$C_{1-6}$alkyl, $C_{6-10}$aryl$C_{2-6}$alkenyl, heteroaryl$C_{2-6}$alkenyl, $C_{6-10}$aryl, heteroaryl or heterocyclyl, optionally substituted as described previously. Typically, $R^3$ represents $C_{1-6}$alkyl which is optionally substituted with up to 3 halogen atoms (such as ethyl, n-propyl, n-butyl and 2,2,2-trifluoroethyl); $C_{2-6}$alkenyl (such as vinyl or allyl); phenyl optionally bearing up to 3 substituents selected from halogen, CN, $NO_2$ and $C_{1-6}$alkyl; and heteroaryl optionally bearing up to 3 substituents selected from halogen, CN, $NO_2$ and $C_{1-6}$alkyl. Suitable heteroaryl groups include optionally substituted pyridine, thiophene, thiazole and isothiazole rings. Preferred embodiments of $R^3$ include n-propyl, n-butyl, phenyl, 2-fluorophenyl, 3-fluorophenyl, 4-fluorophenyl, 2,4-difluorophenyl, 4-chlorophenyl, 2-thienyl, 5-chloro-2-thienyl, 5-bromo-2-thienyl, 3-pyridyl, 6-chloro-2-pyridyl and 5-isothiazolyl. Most preferably, $R^3$ represents 5-chloro-2-thienyl.

$R^4$ represents H, halogen, Ar, heterocyclyl, CN, —$OR^9$, —$N(R^9)_2$, —$N(R^9)COR^{10}$, —$N(R^9)CO_2R^{10}$, —$OCOR^{10}$, —$COR^9$, —$C(=NOR^{11})R^9$, —$CO_2R^9$, —$OCO_2R^{10}$, —$OSO_2R^9$, —$OSO_2N(R^9)_2$, —$CON(R^9)_2$, —$OCON(R^9)_2$, or —$CSN(R^9)_2$; while $L_1$ represents a covalent bond, $C_{1-6}$alkylene, $C_{2-6}$alkenylene, $C_{2-6}$alkynylene or $C_{1-4}$alkylene-W—$C_{1-4}$alkylene where W represents O, S, $SO_2$, NH, NH—CO—NH, O—CO—O, O—CO—NH or NH—CO—O, any of the alkylene groups optionally being substituted by halogen, CN, hydroxyl or $C_{1-4}$alkoxy; provided that if $R^4$ represents H, then $L_1$ does not represent a covalent bond.

Typical embodiments of $R^4$ include H, $OR^9$, $N(R^9)_2$, $CON(R^9)_2$, $OCON(R^9)_2$, CHO, CH═NOH, $CO_2R^9$, Ar, CN, Br, $OSO_2NH_2$ and heterocyclyl, where $R^9$ and Ar are as defined previously. $R^9$ is typically H or $C_{1-6}$alkyl, or two $R^9$ groups attached to the same nitrogen complete a heterocyclic ring as defined previously. Examples of rings represented by $N(R^9)_2$ include piperidine, 4-hydroxypiperidine, 4-hydroxymethylpiperidine, 4-carbamoylpiperidine, 3-carbamoylpiperidine, morpholine, pyrrolidine, 2-pyrrolidone, imidazole and 2-imidazolidone.

Typical embodiments of $L_1$ include covalent bond, $CH_2$, $CH_2CH_2$, CH═CH, CH═$CHCH_2$, $CH_2$—W—$CH_2$, $CH_2$—W—$CH_2CH_2$ and $CH_2$—W—$CH_2CH_2CH_2$, where W is as defined previously. (Throughout, embodiments of $L_1$ are written with the ring attachment point on the left and the attachment point for $R^4$ on the right, and an analogous convention is used for W). Preferred embodiments of W include —O— and —OCONH—.

A subset of the compounds of formula I are in accordance with formula II:

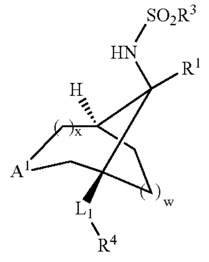

II where $A^1$ represents —$CH_2$—, —$CH_2CH_2$—, —CH═CH— or

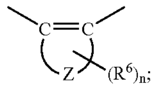

and n, w, x, Z, $L_1$, $R^1$, $R^3$, $R^4$ and $R^6$ have the same meanings as before.

Representative compounds of formula II include those in which w is 1, x is 1, $R^1$ is H, $R^3$ is 5-chloro-2-thienyl and $A^1$, $L_1$ and $R^4$ are as indicated in the following table:

| $A^1$ | $L_1$ | $R^4$ |
|---|---|---|
| ortho-phenylene | bond | OH |
| ortho-phenylene | $CH_2$ | OH |
| ortho-phenylene | $CH_2$ | OCOMe |
| ortho-phenylene | $CH_2$ | $NH_2$ |
| ortho-phenylene | bond | $NH_2$ |
| ortho-phenylene | bond | Br |
| ortho-phenylene | $CH_2$ | $OSO_2NH_2$ |
| $CH_2CH_2$ | $CH_2$ | OH |
| $CH_2CH_2$ | CH═$CHCH_2$ | OH |
| $CH_2CH_2$ | $CH_2CH_2$ | $CONH_2$ |
| $CH_2CH_2$ | $CH_2$ | 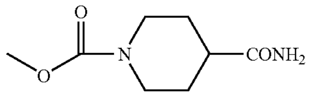 |
| $CH_2CH_2$ | bond | CHO |
| $CH_2CH_2$ | $CH_2$ | 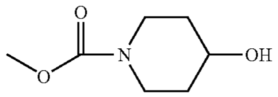 |
| $CH_2CH_2$ | bond | CH═N—OH |
| $CH_2CH_2$ | $CH_2$ | 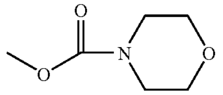 |
| $CH_2CH_2$ | bond | $CSNH_2$ |
| $CH_2CH_2$ | bond | $CO_2Et$ |
| $CH_2CH_2$ | CH(OH) | Ph |
| $CH_2CH_2$ | $CH_2$ | OMe |
| $CH_2CH_2$ | bond | CN |

-continued

| $A^1$ | $L_1$ | $R^4$ |
|---|---|---|
| $CH_2CH_2$ | $CH_2$ | 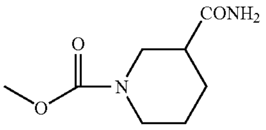 |
| $CH_2CH_2$ | CH=CH | $CO_2Et$ |
| $CH_2CH_2$ | $CH_2$—OCONH—$(CH_2)_3$ | morpholin-4-yl |
| $CH_2CH_2$ | $CH_2$ | 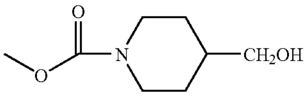 |
| $CH_2CH_2$ | $CH_2$—OCONH—$CH_2CH_2$ | 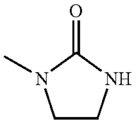 |
| $CH_2CH_2$ | CH=CH | $CONH_2$ |
| $CH_2CH_2$ | bond | $NHCO_2{}^tBu$ |
| $CH_2CH_2$ | $CH_2$—O—$CH_2$ | 4-methoxyphenyl |
| $CH_2CH_2$ | CH=CH | $CO_2H$ |
| $CH_2CH_2$ | bond | $CONH_2$ |
| $CH_2CH_2$ | $CH_2OCH_2$ | Ph |
| $CH_2CH_2$ | bond | $NHCH_2CO_2Me$ |
| $CH_2CH_2$ | bond | 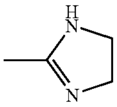 |
| CH=CH | bond | $CO_2Et$ |
| CH=CH | $CH_2$ | OH |
| CH=CH | bond | CONHMe |
| $CH_2$ | $CH_2$—OCONH—$CH_2CH_2$ | 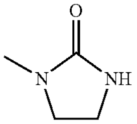 |
| $CH_2$ | $CH_2$—O—$CH_2CH_2$ | morpholin-4-yl |
| $CH_2$ | $CH_2$ | OH |
| $CH_2$ | $CH_2$—OCONH—$(CH_2)_3$ | 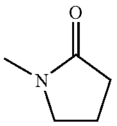 |
| $CH_2$ | $CH_2$—OCONH—$(CH_2)_3$ | H |
| $CH_2$ | $CH_2$—OCONH—$CH_2CH_2$ | 2-pyridyl |
| $CH_2$ | $CH_2$—OCONH—$(CH_2)_3$ | morpholin-4-yl |
| $CH_2$ | bond | $CO_2Me$ |
| $CH_2$ | $CH_2$—OCONH—$CH_2CH_2$ | morpholin-4-yl |
| $CH_2$ | $CH_2$—OCONH—$(CH_2)_4$ | H |
| $CH_2$ | $CH_2$ | MeO |
| $CH_2$ | $CH_2$—OCONH—$(CH_2)_3$ | imidazol-1-yl |

The invention provides pharmaceutical compositions comprising one or more compounds of formula I and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycol, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of formula I or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of formula I or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to formula I or a pharmaceutically acceptable salt thereof.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, poly(vinylpyrrolidone) or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

The compounds of formula I may be prepared by a process comprising the steps of:

(a) bis-alkylation of ketoesters (1) with G-A-G (or, alternatively, bis-alkylation of ketoesters (2) with G-B-G) to form the bridged bicyclic ketones (3):

(1)

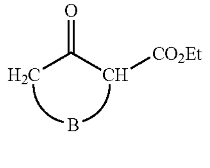

-continued (2)

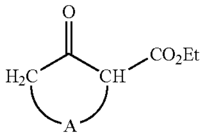

(3)

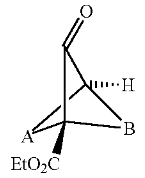

(b) conversion of the ketones (3) to the oximes (4) and reduction of same to the amines (5):

(4)

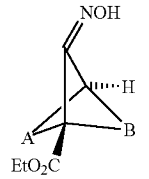

(5)

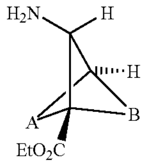

and (c) reaction of amines (5) with $R^3SO_2Cl$ to form sulphonamides (6):

(6)

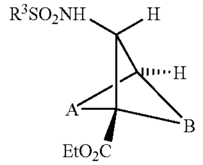

where G represents a leaving group such as chloride, bromide, iodide, mesylate or tosylate (especially bromide), and A, B and $R^3$ have the same meanings as before. The bisalkylation of (1) or (2) is typically performed in a solvent such as THF or DMF in the presence of strong base such as sodium hydride, sodium ethoxide or lithium diisopropylamide, the last-named being particularly suitable for the second stage of the bisalkylation. The oximes (4) may be formed by reaction of ketones (3) with hydroxylamine in refluxing ethanol, and may be reduced to the corresponding amines (5) by sequential treatment with sodium cyanoborohydride and zinc/acetic acid. Reaction of the amines (5) with $R^3SO_2Cl$ to form sulphonamides (6) takes place in an inert solvent in the presence of a base such as triethylamine.

Alternatively, the sulphonamides (6) may be obtained by reduction of the sulphonylimines (4a):

(4a)

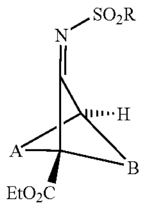

where A, B and $R^3$ have the same meanings as before. The reduction is typically carried out by treatment with sodium borohydride in alcoholic solution at about 0° C. The sulphonylimines (4a) are available by condensation of ketones (3) with sulphonamides $R^3SO_2NH_2$, which is typically carried out in refluxing toluene with azeotropic removal of water.

The sulphonamides (6) are compounds of formula I in which $R^1$ and $R^2$ are both H, $L_1$ is a covalent bond and $R^4$ is $CO_2Et$. Corresponding compounds in which $R^1$ is alkyl or are accessible by reaction of sulphonylimines (4a) with the appropriate organolithium $R^1Li$, e.g at reduced temperature in a hydrocarbon solvent with subsequent quenching with dilute aqueous acid. Corresponding compounds in which $R^2$ is other than H may be obtained by alkylation or acylation of (6) by standard methods. Alternatively, the amines (5) may be N-monoalkylated by conventional procedures prior to reaction with $R^3SO_2Cl$.

The ethoxycarbonyl group in the sulphonamides (6) may be converted into other functionalities in accordance with formula I using conventional techniques of organic synthesis. For example, hydrolysis with aqueous alkali provides the corresponding carboxylic acids (7) ($R{=}CO_2H$), which in turn may be coupled with amines $(R^9)_2NH$ to provide the amides (7) ($R{=}CON(R^9)_2$):

(7)

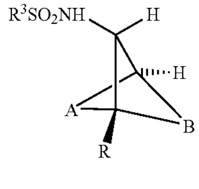

where A, B, $R^3$ and $R^9$ have the same meanings as before. Any of the well known amide-forming processes may be used, such as conversion of the acid to the acid chloride followed by reaction with the amine, and the use of coupling agents such as carbodiimides, dimethylaminopyridine and hydroxybenzotriazole. The amides may be converted to the corresponding thioamides (7) ($R{=}CSN(R^9)_2$) by treatment with Lawesson's reagent, or they may be reduced using aluminium hydride in refluxing THF to provide the amines (7) ($R{=}CH_2N(R^9)_2$, which may in turn be alkylated or acylated by conventional methods if at least one of the $R^9$ groups is H. Primary amides (7) ($R{=}CONH_2$) may be converted to the nitriles (7) (R=CN) by treatment with phosphoryl chloride, and sequential treatment of the nitriles with gaseous HCl in methanol and 1,2-ethylenediamine gives the imidazolines (7) (R=2-imidazolinyl).

The carboxylic acids (7) ($R{=}CO_2H$) alternatively may be converted to the bromides (7) (R=Br) by a process involving their conversion to the acid chlorides by treatment with oxalyl chloride, followed by reaction with N-hydroxypyridin-2-thione sodium salt and bromotrichloromethane under UV irradiation. A further useful transformation of the aforesaid acids is a Curtius-type reaction involving treatment with diphenylphosphorazidate and t-butanol to form the carbamates (7) (R=NHBoc) which are readily cleaved with anhydrous acid to the primary amines (7) ($R{=}NH_2$), and these in turn may be alkylated or acylated using conventional procedures.

Further useful elaborations of the esters (6) involve reduction (e.g. using lithium aluminium hydride) to the primary alcohols (7) ($R{=}CH_2OH$). These may be alkylated or acylated by conventional-methods, and in particular may be treated with phosgene or its equivalent to provide chloroformates (7) ($R{=}CH_2OCOCl$), which in turn may be reacted with amines such as $HN(R^9)_2$ and $HN(R^9)(CH_2)_{1-4}R^4$ to provide carbamates (7) ($R{=}CH_2OCON(R^9)_2$ or $CH_2OCON(R^9)(CH_2)_{1-4}R^4$), where $R^4$ and $R^9$ have the same meanings as before. Alternatively, the alcohols (7) ($R{=}CH_2OH$) may be oxidised to the aldehydes (7) (R=CHO), which may be converted to the oximes (7) (R=CH=NOH), or reacted with $R^{4a}Li$ or $R^{4a}MgBr$ to give secondary alcohols (7) ($R{=}CH(OH)R^{4a}$) where $R^{4a}$ represents Ar, $C_{1-5}$alkyl, $C_{2-5}$alkenyl, or $C_{2-5}$alkynyl.

A further useful reaction of the aldehydes (7) (R=CHO) is condensation with ylides to form alkenes. In particular, condensation with diethylphosphonoacetic acid ethyl ester in the presence of strong base provides the unsaturated esters (7) ($R{=}CH{=}CHCO_2Et$). The olefinic group may be reduced to the corresponding saturated analogue by hydrogenation in the presence of a rhodium or platinum catalyst, while the ester group may be subjected to any of the transformations already described in connection with compounds (6).

In addition to the manipulations of the bridgehead substituent outlined above, individual compounds of formula I prepared by the routes described above may be converted into different compounds in accordance with formula I through the application of known synthetic techniques. For example, when $R^3$ or A in formula I comprises a phenyl or heteroaromatic ring, reactions may be carried out on the compounds of formula I (or their precursors) so as to introduce one or more substituents to said rings, or to transform substituents already present thereon.

Where they are not themselves commercially available, the starting materials and reagents employed in the above-described synthetic schemes may be obtained by the application of standard techniques of organic synthesis to commercially available materials.

It will be appreciated that many of the above-described synthetic schemes may give rise to mixtures of stereoisomers. Such mixtures may be separated by conventional means such as fractional crystallisation and preparative chromatography.

Certain compounds according to the invention may exist as optical isomers due to the presence of one or more chiral centres or because of the overall asymmetry of the molecule. Such compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50–70% confluency in the presence of sterile 10 mM sodium butyrate.

(2) Cells are placed in 96-well plates at 30,000/well/100 μL in minimal essential medium (MEM)(phenol red-free)+10% foetal bovine serum (FBS), 50 mM HEPES buffer (pH7.3), 1% glutamine, 0.2 mg/ml G418 antibiotic, 10 mM sodium butyrate.

(3) Make dilutions of the compound plate. Dilute stock solution to 5.5% DMSO/110 μM compound. Mix compounds vigorously and store at 4° C. until use.

(4) Add 10 μL compound/well. Mix plate briefly, and leave for 18 h in 37° C. incubator.

(5) Remove 90 μL of culture supernatant and dilute 1:1 with ice-cold 25 mM HEPES (pH.3), 0.1% BSA, 1.0 mM EDTA (+broad spectrum protease inhibitor cocktail; pre-aliquotted into a 96-well plate). Mix and keep on ice or freeze at −80° C.

(6) Add back 100 μL of warm MEM+10% FBS, 50 mM HEPES (pH7.3), 1% glutamine, 0.2 mg/ml G418, 10 mM sodium butyrate to each well, and return plate to 37° C. incubator.

(7) Prepare reagents necessary to determine amyloid peptide levels, for example by ELISA assay.

(8) To determine if compounds are cytotoxic, cell viability following compound administration is assessed by the use of redox dye reduction. A typical example is a combination of redox dye MTS (Promega) and the electron coupling reagent PES. This mixture is made up according to the manufacturer's instructions and left at room temperature.

(9) Quantitate amyloid beta 40 and 42 peptides using an appropriate volume of diluted culture medium by standard ELISA techniques.

(10) Add 15 μL/well MTS/PES solution to the cells; mix and leave at 37° C.

(11) Read plate when the absorbance values are approximately 1.0 (mix briefly before reading to disperse the reduced formazan product).

Alternative assays are described in *Biochemistry,* 2000, 39(30), 8698–8704.

The Examples of the present invention all had an $ED_{50}$ of less than 10 μM, preferably less than 1 μM and most preferably less than 100 nM in at least one of the above assays.

The following examples illustrate the present invention.

The following is an explanation of abbreviations used in the Examples:

| | |
|---|---|
| DMF | N,N-dimethylformamide |
| LDA | lithium diisopropylamide |
| THF | tetrahydrofuran |
| DCM | dichloromethane |
| DMAP | 4-(dimethylamino)pyridine |
| BOC | t-butoxycarbonyl |
| m-CPBA | m-chloroperoxybenzoic acid |

EXAMPLE 1

5-Chloro-N-[(6R/S,9R/S,11S/R)-6-(hydroxymethyl)-5,6,7,8,9,10-hexahydro-6,9-methanobenzo[α][8]annulen-11-yl]thiophene-2-sulfonamide

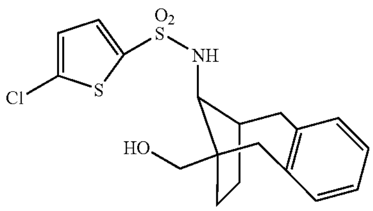

(1) To ethyl cyclopentanone-2-carboxylate (10 g) in DMF (150 ml) at 0° C. under nitrogen was added sodium ethoxide (4.6 g) portionwise over 15 mins.

The mixture was stirred at this temperature for a further 15 mins before adding o-xylylene dibromide (18.6 g) portionwise over 20 mins., allowing to warm to room temperature and stirring overnight. After dilution with water, extraction with ether (×2), washing the combined ethereal phases with NaOH (1M), water and brine, drying and concentration, column chromatography on silica eluting with 20% ether/hexane gave ethyl 1-[2-(bromomethyl)benzyl]-2-oxocyclopentanecarboxylate as an oil (4.3 g, 20%).

(360 MHz $^1H$, $CDCl_3$) 1.23 (3H, t, J=7.2), 1.73–2.11 (4H, m), 2.46 (2H, m), 3.29 (1H, d, J=14.9), 3.42 (1H, d, J=14.9), 4.16 (2H, m), 4.56 (2H, m), 7.10 (1H, m), 7.20 (2H, m), 7.34 (1H, m).

(2) To LDA (1.05 eq) in THF (450 ml) at −78° C. under nitrogen was added ethyl 1-[2-(bromomethyl)benzyl]-2-oxocyclopentanecarboxylate (8.2 g) in THF (50 ml) dropwise over 15 mins. After 45 mins at this temperature, the reaction was allowed to warm to room temperature, quenched with saturated $NH_4Cl$ and extracted with ether (×2), dried and concentrated. Column chromatography on silica eluting with 20–30% ether/hexane gave ethyl (6R/S,9R/S)-11-oxo-7,8,9,10-tetrahydro-6,9-methanobenzo[α][8]annulene-6(5H)-carboxylate as an oil which crystallised on standing (2.3 g, 37%).

(360 MHz $^1H$, $CDCl_3$) 1.27 (1H, m), 1.31 (3H, t, J=7.1), 1.57 (1H, m), 1.98 (1H, m), 2.40 (1H, dt, J=4.4, 13.2), 2.78 (1H, m), 2.98 (2H, m), 3.29 (1H, d, J=14.9), 3.42 (1H, d, J=14.9), 4.26 (2H, q, J=7.1), 7.21 (4H, m).

(3) A mixture of the product of step (2) (2.0 g), hydroxylamine hydrochloride (1.61 g) and sodium acetate (3.16 g) in THF (100 ml) was heated to reflux for 1.25 hrs. The reaction was concentrated, water added and then extracted with DCM (3×), dried and evaporated to give an oil (2.1 g, 100%) which was dissolved in acetic acid (30 ml).

Platinum oxide (200 mg) was introduced and the mixture hydrogenolysed under a balloon of hydrogen for 16 hrs. After filtering, concentrating and adding sodium hydroxide, extraction with DCM (3×), drying and concentration gave a pale yellow oil (2.0 g, 100%). The resulting amine (2.0 g) was added to a mixture of 5-chlorothiophene sulfonyl chloride (2.1 g) and triethylamine (1.35 g) in DCM (50 ml) at 0° C. under nitrogen and stirred for 16 hrs at room temperature. Addition of water, extraction with DCM (3×), drying, concentration and column chromatography on silica eluting with 5% DCM in 10% EtOAc/hexane gave ethyl (6R/S,9R/S,11S/R)-11-{[(5-chlorothien-2-yl)sulfonyl]amino}-7,8,9,10-tetrahydro-6,9-methanobenzo[α][8]annulene-6(5H)-carboxylate as a white powder (2.2 g, 65%).

(360 MHz $^{1}$H, $CDCl_3$) 1.19 (1H, m), 1.24 (3H, t, J=7.2), 1.42 (1H, m), 1.74 (1H, m), 1.97 (1H, dt, J=4.5, 13.1), 2.55 (1H, dd, J=8, 15.9), 2.69 (1H, dd, J=7.4, 14.6), 2.86 (1H, d, J=15.9), 3.30 (1H, d, J=15.9), 3.38 (1H, d, J=15.9), 3.83 (1H, t, 5.5), 4.06 (2H, m), 5.54 (1H, d, J=4.6), 6.94 (1H, d, J=4), 7.10 (4H, m), 7.44 (1H, d, J=4); (360 MHz $^{13}$C $CDCl_3$) 15.9, 26.7, 32.1, 36.0, 39.5, 40.1, 54.4, 63.3, 64.6, 128.0, 128.5, 128.6, 133.2, 133.5, 133.7, 138.97, 138.3, 140.4, 141.5, 177.7; MS (ES+): M–OEt 394.

(4) To a solution of the product of step (3) (1 g) in THF (40 ml) cooled to 0° C. was added $LiAlH_4$ (1M, 2.39 ml) dropwise. The mixture was stirred at room temperature for 2 hrs, worked-up with water/NaOH then concentrated. Water (20 ml) was added and extraction with EtOAc (3×20 ml), drying, concentration and column chromatography on silica eluting with 20% EtOAc/hexane gave 5-chloro-N-[(6R/S,9R/S,11S/R)-6-(hydroxymethyl)-5,6,7,8,9,10-hexahydro-6,9-methanobenzo[α][8]annulen-11-yl]thiophene-2-sulfonamide as a white solid (0.76 g, 90%).

(360 MHz $^{1}$H, $CDCl_3$) 1.13 (2H, m), 1.58 (2H, m), 2.20 (1H, d, J=15.7), 2.35 (1H, m), 2.58 (1H, dd, J=7.7, 16.1), 2.98 (1H, d, J=15.9), 2.57 (1H, m), 3.04 (1H, d, J=16.2), 3.42 (1H, d, J=11.2), 3.63 (1H, d, J=11.2), 3.70 (1H, dd, J=6.7, 6.8), 5.47 (1H, d, J=7.6), 6.95 (1H, d, J=3.7), 7.07 (4H, m), 7.46 (1H, d, J=3.6); MS (ES+): MH+ 398.

EXAMPLE 2

[(6R/S,9R/S,11S/R)-11-{[(5-Chlorothien-2-yl)sulfonyl]amino}-7,8,9,10-tetrahydro-6,9-methanobenzo[α][8]annulen-6(5H)-yl]methyl acetate

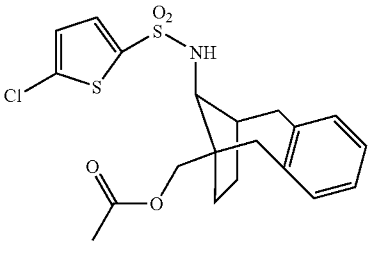

To a solution of the alcohol from Example 1 (67 mg) in DCM (2 ml) at room temperature were added acetyl chloride (13 μl), pyridine (13 μl) and DMAP (1 mg). The mixture was stirred at room temperature for 16 hrs., then washed with 1 M HCl (2 ml) and brine (2 ml). Drying, concentration and column chromatography on silica eluting with 10% EtOAc/hexane gave [(6R/S,9R/S,11S/R)-11-{[(5-chlorothien-2-yl)sulfonyl]amino}-7,8,9,10-tetrahydro-6,9-methanobenzo[α][8]annulen-6(5H)-yl]methyl acetate as a white powder (30 mg, 45%).

(360 MHz $^{1}$H, $CDCl_3$) 1.19 (2H, m), 1.47 (1H, m), 1.67 (1H, m), 2.06 (3H, s), 2.32 (1H, d, J=14.3), 2.48 (1H, m), 2.57 (1H, m), 2.94 (1H, d, J=14.3), 3.15 (1H, d, J=14.3), 3.69 (1H, dd, J=6.3, 6.3), 3.87 (1H, d, J=10.0), 3.96 (1H, d, J=10), 5.31 (1H, d, J=6.9), 6.93 (1H, d, J=3.6), 7.08 (4H, m), 7.44 (1H, d, J=3.6); (360 MHz $^{13}$C $CDCl_3$) 20.8, 24.4, 28.9, 34.6, 38.3, 38.4, 45.2, 61.4, 69.4, 126.3, 126.5, 126.7, 131.5, 131.51, 131.7, 137.5, 137.51, 139.0, 139.5, 170.8; MS (ES+): M+Na 440.

EXAMPLE 3

N-[(6S/R,9R/S,11S/R)-6-(Aminomethyl)-5,6,7,8,9,10-hexahydro-6,9-methanobenzo[α][8]annulen-11-yl]-5-chlorothiophene-2-sulfonamide hydrochloride

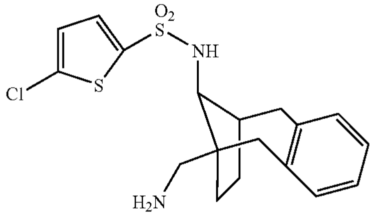

(1) (6R/S,9R/S,11S/R)-11-{[(5-chlorothien-2-yl)sulfonyl]amino}-7,8,9,10-tetrahydro-6,9-methanobenzo[α][8]annulene-6(5H)-carboxylic acid was obtained by alkaline hydrolysis of the ethyl ester from Example 1, step (3). To a suspension of this acid (200 mg) in benzene (6 ml) was added oxalyl chloride (51 μl) and stirred for 2 hrs at room temperature. The mixture was concentrated in vacuo and the residue dissolved in DCM (10 ml), cooled to 0° C. and bubbled with ammonia for 10 mins. Stirring for 1 hr at room temperature, followed by concentration and trituration with ether gave (6R/S,9R/S,11S/R)-11-{[(5-chlorothien-2-yl)sulfonyl]amino}-7,8,9,10-tetrahydro-6,9-methanobenzo[α][8]annulene-6(5H)-carboxamide as a white powder (130 mg, 65%).

(2) The amide from Step (1) (100 mg) in THF (3 ml) was treated with alane (3 eq) then heated to reflux for 30 mins. Cooling to 0° C., followed by a standard work-up using water/NaOH/water gave a gummy solid (65 mg, 67%). A small quantity was treated with HCl in ether/MeOH to give N-[(6S/R,9R/S,11S/R)-6-(aminomethyl)-5,6,7,8,9,10-hexahydro-6,9-methanobenzo[α][8]annulen-11-yl]-5-chlorothiophene-2-sulfonamide hydrochloride as a white powder.

(360 MHz $^{1}$H $d_6$-DMSO) 0.85 (1H, m), 1.07 (1H, m), 1.45 (1H, m), 1.62 (1H, m), 2.10 (1H, m), 2.39 (1H, m), 2.62 (1H, d, J=15.8), 2.70 (1H, m), 2.86 (1H, m), 2.90 (1H, d, J=15.6), 3.17 (1H, d, J=15.7), 3.61 (1H, dd, J=6.7, 8.6), 7.08 (3H, m), 7.15 (1H, m), 7.30 (1H, d, J=4.0), 7.59 (1H, d, J=4.0), 7.98 (3H, brs), 8.52 (1H, d, J=9.4); MS (ES+): MH+ 397.

EXAMPLE 4

N-[(6R/S,9R/S,11S/R)-6-Amino-5,6,7,8,9,10-hexahydro-6,9-methanobenzo[α][8]annulen-11-yl]-5-chlorothiophene-2-sulfonamide hydrochloride

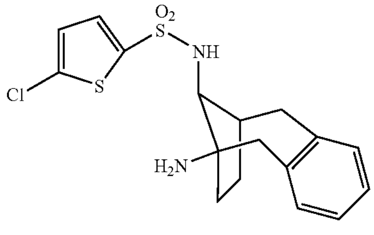

(1) A mixture of the acid from Example 3, Step (1) (84 mg), diphenylphosphoryl azide (44 μl) and $Et_3N$ (28 μl) in toluene (2 ml) was heated to reflux for 2.5 hrs. After concentration in vacuo, addition of t-butanol (2 ml) and heating to reflux for 18 hrs., the mixture was evaporated, treated with saturated aqueous $NaHCO_3$ (5 ml) and extracted with DCM (3×5 ml). Drying, concentration and column chromatography on silica eluting with 10% EtOAc/hexanes gave tert-butyl (6R/S,9R/S,11S/R)-11-{[(5-chlorothien-2-yl)sulfonyl]amino}-7,8,9,10-tetrahydro-6,9-methanobenzo[α][8]annulen-6(5H)-ylcarbamate as a white solid (47 mg, 48%).

(2) A solution of the BOC-derivative from Step (1) (37 mg) in ether (10 ml) at 0° C. was bubbled HCl gas for 10 mins, then left at room temperature for 45 mins. Concentration in vacuo and treatment with ethereal HCl, then trituration with ether, gave N-[(6R/S,9R/S,11S/R)-6-amino-5,6,7,8,9,10-hexahydro-6,9-methanobenzo[α][8]annulen-11-yl]-5-chlorothiophene-2-sulfonamide hydrochloride as a white powder (33 mg, 100%).

(360 MHz $^1H$ $d_6$-DMSO) 0.90 (1H, m), 1.36 (1H, m), 1.69 (2H, m), 2.15 (1H, m), 2.40 (1H, dd, 7.8, 15.98), 2.64 (1H, d, J=15.3), 3.14 (1H, d, J=15.9), 3.42 (1H, d, J=15.5), 3.91 (1H, brm), 7.12 (4H, m), 7.32 (1H, d, J=4.1), 7.63 (1H, d, J=4.0), 8.36 (3H, brs), 8.78 (1H, brm); MS (ES+): MH+ 383.

EXAMPLE 5

N-[(6R/S,9R/S,11S/R)-6-Bromo-5,6,7,8,9,10-hexahydro-6,9-methanobenzo[α][8]annulen-11-yl]-5-chlorothiophene-2-sulfonamide

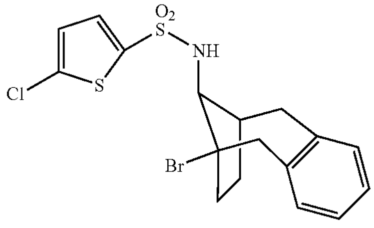

To a suspension of (6R/S,9R/S,11S/R)-11-{[(5-chlorothien-2-yl)sulfonyl]amino}-7,8,9,10-tetrahydro-6,9-methanobenzo[α][8]annulene-6(5H)-carboxylic acid (example 3, Step (1)) (100 mg) in benzene (3 ml) were added oxalyl chloride (74 μl) and DMF (1 drop) at room temperature and the mixture stirred for 2 hrs. After concentration in vacuo, the residue was redissolved in benzene (3 ml) and added dropwise to a refluxing suspension of N-hydroxypyridin-2-thione sodium salt (43 mg) in $CBrCl_3$ (4 ml) whilst irradiating with a 250 W lamp for 1 hr. Concentration and purification using HPLC gave N-[(6R/S,9R/S,11S/R)-6-bromo-5,6,7,8,9,10-hexahydro-6,9-methanobenzo[α][8]annulen-11-yl]-5-chlorothiophene-2-sulfonamide as a white solid (54 mg, 50%).

(360 MHz $^1H$, $CDCl_3$) 1.19 (1H, m), 1.88 (1H, m), 2.01 (1H, m), 2.24 (1H, m), 2.60 (2H, m), 3.22 (1H, d, J=13.9), 3.37 (1H, d, J=14.2), 3.61 (1H, d, J=14.3), 3.89 (1H, dd, J=5.0, 5.0), 5.14 (1H, d, J=3.9), 6.97 (1H, d, J=3.6), 7.11 (4H, m), 7.50 (1H, d, J=3.6); MS (ES+): M+Na 446.

EXAMPLE 6

5-Chloro-N-[(6R/S,9R/S,11S/R)-6-hydroxy-5,6,7,8,9,10-hexahydro-6,9-methanobenzo[α][8]annulen-11-yl]thiophene-2-sulfonamide

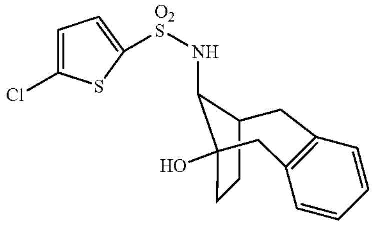

(1) A solution of the carboxylic acid of Example 3, Step (1) (215 mg) in THF (10 ml) was cooled to 0° C. and oxalyl chloride (1.0 ml) was added. The reaction was stirred for 1 h at room temperature then at 60° C. for 0.5 h. The reaction was concentrated in vacuo then dissolved in THF (5 ml) and cooled to 0° C. Dimethylhydroxylamine hydrochloride (56 mg) and pyridine (0.1 ml) were added and the reaction was stirred at room temperature for 2 h. The reaction was quenched with water (10 ml), extracted with EtOAc, washed with 2N NaOH (10 ml), 1M HCl (10 ml) and brine (10 ml), dried over $MgSO_4$ and concentrated in vacuo. (6R/S,9R/S,1S/R)-11-{[(5-Chlorothien-2-yl)sulfonyl]amino}-N-methoxy-N-methyl-7,8,9,10-tetrahydro-6,9-methanobenzo[α][8]annulene-6(5H)-carboxamide was purified by column chromatography (silica, 25–40% EtOAc in hexane) to give a white solid (109 mg, 46%).

(2) Methyl magnesium chloride (0.32 ml, 3M in THF) was added to a solution of the amide from Step (1) (109 mg) in THF (5 ml) was heated under reflux for 3 h. The reaction was quenched with water (10 ml), extracted with EtOAc, washed with brine (10 ml), dried over $MgSO_4$ and concentrated in vacuo. Purification by column chromatography (silica, 20% EtOAc in hexane) gave N-[(6R/S,9R/S,11S/R)-6-acetyl-5,6,7,8,9,10-hexahydro-6,9-methanobenzo[α][8]annulen-11-yl]-5-chlorothiophene-2-sulfonamide as a white solid (72 mg, 73%).

(3) The product of Step (2) (72 mg) and m-CPBA (180 mg) in DCM (10 ml) were heated under reflux for 16 h. Another portion of m-CPBA (180 mg) and sodium bicar bonate (16 mg) were added and the reaction heated under reflux for 64 h. The reaction was diluted with sodium bicarbonate solution (10 ml), extracted with DCM, washed with brine (10 ml), dried over-$MgSO_4$ and concentrated in vacuo. Purification by column chromatography (silica, 10–15% EtOAc in hexane) gave (6R/S,9R/S,11S/R)-11-{[(5-chlorothien-2-yl)sulfonyl]amino}-7,8,9,10-tetrahydro-6,9-methanobenzo[α][8]annulen-6(5H)-yl acetate as a white solid (24 mg, 32%).

(4) To a solution of the acetate from Step (3) (22 mg) in dry THF (2 ml) at 0° C. was added lithium aluminium hydride (1.0M in ether, 0.05 ml). The reaction was stirred at 0° C. for 0.5 h then at room temperature for 0.5 h. The reaction was quenched with 2N HCl (15 ml), extracted with EtOAc, washed with brine, dried over $MgSO_4$ and concentrated in vacuo. The product was purified by column chromatography (silica, 20% EtOAc in hexane) to give 5-chloro-N-[(6R/S,9R/S,11S/R)-6-hydroxy-5,6,7,8,9,10-hexahydro-6,9-methanobenzo[α][8]annulen-11-yl]thiophene-2-sulfonamide as a white solid (15 mg, 76%).

(400 MHz $^1H$, $CDCl_3$) 1.08 (1H, m), 1.62 (2H, m), 1.83 (1H, m), 2.46 (1H, q, J=7.2), 2.52 (1H, s), 2.58 (1H, dd, J=7.7, 16.1), 2.68 (1H, d, J=15.6), 3.04 (1H, d, J=16.1), 3.43 (1H, d, J=15.6), 3.69 (1H, m), 5.10 (1H, d, J=6.1), 6.96 (1H, d, J=4.0), 7.04 (1H, m), 7.11 (3H, m), 7.49 (1H, d, J=4.0).

EXAMPLE 7

[(6R/S,9R/S,11S/R)-11-{[(5-Chlorothien-2-yl)sulfonyl]amino}-7,8,9,10-tetrahydro-6,9-methanobenzo[α][8]annulen-6(5H)-yl]methyl sulfamate

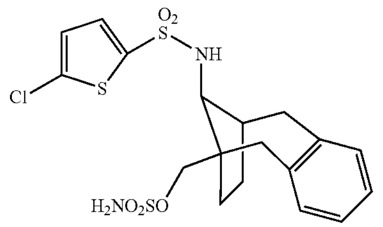

To a solution of the product from Example 1 (67 mg) in DCM (2 ml) at room temperature were added sulfamoyl chloride (19 mg), pyridine (13 μl) and DMAP (1 mg). The mixture was stirred at room temperature for 16 hrs., washed with 1 M HCl (2 ml) and brine (2 ml) and dried. Concentration and column chromatography on silica eluting with 30% EtOAc/hexane gave [(6R/S,9R/S,11S/R)-11-{[(5-chlorothien-2-yl)sulfonyl]amino}-7,8,9,10-tetrahydro-6,9-methanobenzo[α][8]annulen-6(5H)-yl]methyl sulfamate as a white powder (30 mg, 42%).

(360 MHz $^1H$, $CDCl_3$) 1.14 (2H, m), 1.61 (2H, m), 2.15 (1H, m), 2.32 (1H, d, J=14.3), 2.52 (1H, dd, J=6.9, 14.3), 2.95 (2H, m), 3.83 (1H, brm), 4.04 (1H, ABq, J=8.5), 4.12 (1H, ABq, J=8.5), 5.22 (2H, brs), 5.68 (1H, brs), 6.94 (1H, d, J=3.6), 7.08 (4H, m), 7.45 (1H, d, J=3.6); (360 MHz $^{13}C$ $d_6$-DMSO) 26.2, 31.2, 36.1, 38.9, 39.5, 41.1, 47.5, 63.8, 76.7, 128.2, 128.3, 130.0, 133.3, 133.4, 133.8, 136.8, 140.8, 141.9, 143.4; MS (ES+): M+ 477.

EXAMPLE 8

Ethyl (1S/R,6S/R,9S/R)-9-{[(5-chlorothien-2-yl)sulfonyl]amino}bicyclo[4.2.1]nonane-1-carboxylate

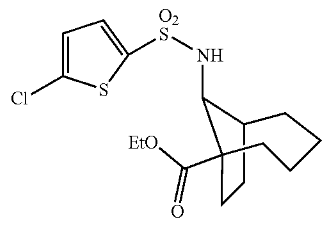

(1) To a solution of ethyl (1S/R,6S/R)-9-oxobicyclo[4.2.1]nonane-1-carboxylate (2.0 g; *J. Am. Chem. Soc.,* 1973, 7413), triethylamine (4.0 ml) and 5-chlorothiophene-2-sulfonamide (3.76 g) in dry DCM (30 ml) at 0° C. was added $TiCl_4$ (1.0M in DCM, 4.8 ml). The reaction was stirred at 0° C. and $TiCl_4$ (1.0M in DCM, 4.8 ml) was added after 1 h and 2 h. After 4 h the reaction was concentrated in vacuo, then dissolved in DCM and washed with saturated sodium bicarbonate, dried over $MgSO_4$ and concentrated in vacuo. The resulting ethyl (1S/R,6S/R,9E)-9-{[(5-chlorothien-2-yl)sulfonyl]imino}bicyclo[4.2.1]nonane-1-carboxylate was purified by column chromatography (silica, 10–25% EtOAc in hexane).

(2) A solution of the imine from Step (1) in EtOH (50 ml) was cooled to 0° C. and $NaBH_4$ (0.36 g) was added portionwise. The reaction was stirred at room temperature for 1 h then concentrated in vacuo. Water was added and the mixture extracted with EtOAc, washed with brine, dried over $MgSO_4$ and concentrated in vacuo. Purification by column chromatography (silica, 10–25% EtOAc in hexane) gave ethyl (1S/R,6S/R,9S/R)-9-{[(5-chlorothien-2-yl)sulfonyl]amino}bicyclo[4.2.1]nonane-1-carboxylate as a white solid (2.49 g, 67%).

(360 MHz $^1H$, $CDCl_3$) 1.20 (3H, t, J=7.1), 1.46–2.07 (11H, m), 2.15–2.23 (1H, m), 2.56–2.58 (1H, m), 3.80 (1H, m), 4.00 (2H, m), 5.00 (1H, d, J=4.4), 6.91 (1H, d, J=4.0), 7.40 (1H, d, J=4.0); ($^{13}C$ $CDCl_3$) 15.9, 25.9, 26.8, 30.4, 32.3, 34.7, 35.6, 41.0, 56.1, 62.9, 64.4, 128.5, 133.7, 139.0, 140.3, 178.4. MS (ES+): [M–OEt]+ 346, [M–$CO_2$Et]+ 318.

EXAMPLE 9

5-Chloro-N-[(1S/R,6S/R,9S/R)-1-(hydroxymethyl)bicyclo[4.2.1]non-9-yl]thiophene-2-sulfonamide

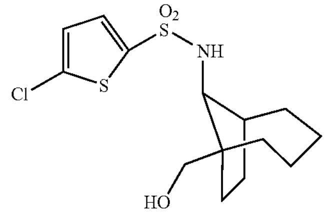

$LiAlH_4$ (1.0M in ether, 4.6 ml) was added dropwise to a solution of the ethyl ester from Example 8 (1.82 g) in ether (40 ml) at 0° C. The reaction was stirred at room temperature for 1 h then cooled to 0° C. and quenched with water. The mixture was diluted with 2N HCl and extracted with EtOAc, washed with brine, dried over $MgSO_4$ and concentrated in vacuo. The product was purified by column chromatography (silica, 25% EtOAc in hexane) to give 5-chloro-N-[(1S/R, 6S/R,9S/R)-1-(hydroxymethyl)bicyclo[4.2.1]non-9-yl] thiophene-2-sulfonamide as a white solid (1.65 g, 100%).

(360 MHz $^1H$, $CDCl_3$) 1.25–1.93 (12H, m), 2.19–2.27 (2H, m), 3.28 (1H, d, J=11.3), 3.48 (1H, d, J=11.3), 3.61–3.65 (1H, m), 4.90 (1H, d, J=8.6), 6.92 (1H, d, J=4.0), 7.42 (1H, d, J=4.0); ($^{13}C$, $CDCl_3$) 25.9, 27.3, 29.9, 31.6, 32.1, 35.6, 40.0, 50.3, 62.1, 69.5, 128.6, 133.5, 139.2, 141.0. MS (ES+): [M−OH]+ 332.

EXAMPLE 10

5-Chloro-N-[(1S/R,6S/R,9S/R)-1-formylbicyclo [4.2.1]non-9-yl]thiophene-2-sulfonamide

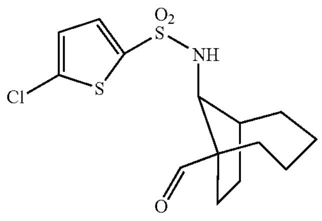

Sulfur trioxide pyridine complex (1.55 g) was added portionwise to a solution of the alcohol from Example 9 (1.05 g) and triethylamine (6.0 ml) in dry DMSO (60 ml). The reaction was stirred at room temperature for 45 min then poured into 2N HCl and extracted with EtOAc. The extracts were washed sequentially with 2N HCl, water and brine, dried over $MgSO_4$ and concentrated in vacuo. Purification by column chromatography (silica, 15–20% EtOAc in hexane) gave 5-chloro-N-[(1S/R,6S/R,9S/R)-1-formylbicyclo [4.2.1]non-9-yl]thiophene-2-sulfonamide as a white solid (0.96 g, 92%).

(400 MHz $^1H$, $CDCl_3$) 1.54–1.88 (10H, m), 1.96–2.01 (2H, m), 2.46–2.49 (1H, m), 3.85 (1H, dd, J=7.7, 7.7), 4.97 (1H, d, J=7.7), 6.93 (1H, d, J=4.0), 7.40 (1H, d, J=4.0), 9.30 (1H, s); ($^{13}C$, $CDCl_3$) 23.9, 24.5, 28.0, 29.8, 30.0, 30.9, 39.7, 57.9, 60.7, 126.8, 132.1, 137.6, 138.7, 202.7.

EXAMPLE 11 tert-Butyl (1S/R,6S/R,9S/R)-9-{[(5-chlorothien-2-yl)sulfonyl]amino}bicyclo[4.2.1]non-1-ylcarbamate

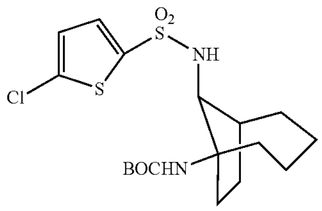

(1) The ethyl ester from Example 8 was heated under reflux in 4N NaOH/THF for 1 hr., then cooled, acidified and extracted with DCM. The extracts were dried over $MgSO_4$ and concentrated in vacuo to give (1S/R,6S/R, 9S/R)-9-{[(5-chlorothien-2-yl)sulfonyl]amino}bicyclo [4.2.1]nonane-1-carboxylic acid in quantitative yield. (2) A solution of the acid (0.120 g), triethylamine (32 mg) and diphenylphosphoryl azide (87 mg) in dry toluene (6 ml) was heated under reflux for 3 hrs. The reaction was concentrated in vacuo, tert-butanol (10 ml) was added and heated under reflux. After 16 h the reaction was concentrated in vacuo, then dissolved in DCM and washed with saturated sodium bicarbonate, dried over $MgSO_4$ and concentrated in vacuo. Purification by column chromatography (silica, 10% EtOAc in hexane) gave tert-butyl (1S/R,6S/R,9S/R)-9-{[(5-chlorothien-2-yl)sulfonyl] amino}bicyclo[4.2.1]non-1-ylcarbamate a white foam (0.067 g, 49%).

(400 MHz $^1H$, $CDCl_3$) 1.40 (9H, s), 1.44–2.04 (12H, m), 2.44 (1H, brs), 3.64 (1H, brm), 4.92 (1H, brs), 6.55 (1H, brs), 6.91 (1H, d, J=4.0), 7.41 (1H, d, J=4.0). MS (ES+): [MH−BOC]+ 335.

EXAMPLE 12

(1S/R,6S/R,9S/R)-9-{[(5-Chlorothien-2-yl)sulfonyl] amino}bicyclo[4.2.1]nonane-1-carboxamide

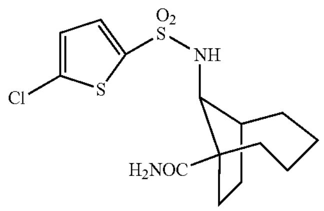

A solution of the carboxylic acid from Example 11 Step (1) (0.82 g) in dry THF (10 ml) was cooled to 0° C. and oxalyl chloride (0.24 ml) was added dropwise. The reaction was stirred for 2 h at room temperature then heated under reflux for 30 min and concentrated in vacuo. The crude acid chloride was dissolved in dry THF (10 ml) and ammonia was bubbled through the solution at 0° C. for 10 min. The mixture was diluted with 4N NaOH, extracted with chloroform, dried over $MgSO_4$ and concentrated in vacuo to give a white solid (0.264 g). The aqueous extract was acidified with 2N HCl and extracted with DCM, dried over $MgSO_4$ and concentrated in vacuo. The residue was suspended in 4N NaOH and re-extracted with 5% MeOH in DCM, dried over $MgSO_4$ and concentrated in vacuo to give (1S/R,6S/R,9S/ R)-9-{[(5-chlorothien-2-yl)sulfonyl]amino}bicyclo[4.2.1] nonane-1-carboxamide as a white solid (0.384 g). Combined product (0.648 g, 79%).

(360 MHz $^1H$, $d_6$-DMSO) 1.04–1.95 (12H, m), 2.43 (1H, brm), 3.73 (1H, m), 6.81 (1H, s), 6.88 (1H, s), 7.21 (1H, d, J=4.0), 7.42 (1H, s), 7.51 (1H, d, J=4.0); ($^{13}C$ $\delta_6$-DMSO) 26.1, 26.3, 30.4, 32.5, 35.6, 36.1, 41.1, 55.8, 63.9, 129.9, 134.1, 180.5. MS (ES+): [M+Na]+ 385, MH+ 363.

EXAMPLE 13

(1S/R,6S/R,9S/R)-9-{[(5-Chlorothien-2-yl)sulfonyl]amino}bicyclo[4.2.1]nonane-1-carbothioamide

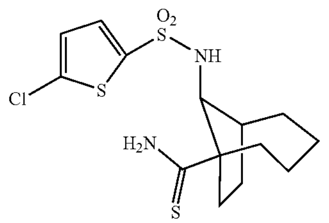

A solution of the amide from Example 12 (0.20 g) and Lawesson's reagent (0.167 g) in dry toluene (6 ml) was heated under reflux for 1 h then concentrated in vacuo. Sodium hydroxide (4N) was added and extracted with DCM, dried over $MgSO_4$ and concentrated in vacuo. Purification by column chromatography (silica, 5% MeOH in DCM) gave (1S/R,6S/R,9S/R)-9-{[(5-chlorothien-2-yl)sulfonyl]amino}bicyclo[4.2.1]nonane-1-carbothioamide as a white solid (0.204, 97%).

(360 MHz $^1$H, $d_6$-DMSO) 1.32–2.18 (12H, m), 2.53 (1H, brm), 3.87 (1H, m), 7.22 (1H, d, J=4.0), 7.48 (1H, d, J=4.0), 7.56 (1H, m), 8.61 (1H, s), 9.54 (1H, s). MS (ES+): MH+ 379.

EXAMPLE 14

5-Chloro-N-[(1S/R,6S/R,9S/R)-1-cyanobicyclo[4.2.1]non-9-yl]thiophene-2-sulfonamide

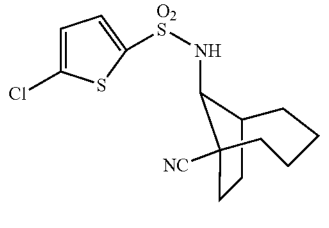

A mixture of the amide from Example 12 (0.19 g) and $POCl_3$ (4.0 ml) was heated under reflux for 1 h. The reaction was concentrated in vacuo and saturated sodium bicarbonate solution was added to the residue. The reaction was extracted with DCM, dried over $MgSO_4$ and concentrated in vacuo then purification by column chromatography (silica, 30% EtOAc in hexane) gave 5-chloro-N-[(1S/R,6S/R,9S/R)-1-cyanobicyclo[4.2.1]non-9-yl]thiophene-2-sulfonamide a white solid (0.15 g, 81%).

(400 MHz $^1$H, $CDCl_3$) 1.50–1.81 (7H, m), 1.87–2.00 (3H, m), 2.05–2.16 (1H, m), 2.22–2.30 (1H, m), 2.46–2.52 (1H, m), 4.01 (1H, dd, J=8.4, 8.4), 5.10 (1H, d, J=8.4), 6.94 (1H, d, J=4.1), 7.52 (1H, d, J=4.1); ($^{13}$C, $CDCl_3$) 23.8, 24.8, 28.4, 29.7, 34.1, 35.1, 38.7, 42.7, 63.7, 123.9, 126.9, 132.5, 138.0, 138.4. MS (ES+): [M+Na]+ 367, MH+ 345.

EXAMPLE 15

5-Chloro-N-[(1S/R,6S/R,9S/R)-1-(methoxymethyl)bicyclo[4.2.1]non-9-yl]thiophene-2-sulfonamide

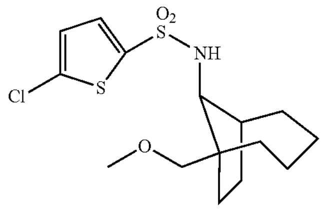

To a suspension of NaH (60% dispersion, 15 mg) in dry THF (5 ml) at 0° C. was added the product from Example 9 (52 mg). The reaction was stirred at 0° C. for 15 min then MeI (0.01 ml) was added. After 3 h at room temperature the reaction was quenched with water and extracted with EtOAc, washed with brine, dried over $MgSO_4$ and concentrated in vacuo. Purification by column chromatography (silica, 20% EtOAc in hexane) gave 5-chloro-N-[(1S/R,6S/R,9S/R)-1-(methoxymethyl)bicyclo[4.2.1]non-9-yl]thiophene-2-sulfonamide a white solid (36 mg, 67%).

(400 MHz $^1$H, $CDCl_3$) 1.46–1.65 (10H, m), 1.83–1.89 (2H, m), 2.46 (1H, brm), 2.95 (1H, d, J=8.7), 3.10 (1H, d, J=8.7), 3.18 (3H, s), 3.35–3.38 (1H, m), 5.09 (1H, d, J=4.5), 6.93 (1H, d, J=4.0), 7.38 (1H, d, J=4.0); ($^{13}$C, $CDCl_3$) 26.3, 26.7, 29.9, 32.2, 34.1, 36.0, 41.3, 49.4, 60.8, 65.2, 83.1, 128.3, 133.4, 138.7, 140.6. MS (ES+): MH+ 364, [M–OMe]+ 332.

EXAMPLE 16

Ethyl(2E)-3-((1R/S,6S/R,9S/R)-9-{[(5-chlorothien-2-yl)sulfonyl]amino}bicyclo[4.2.1]non-1-yl)prop-2-enoate

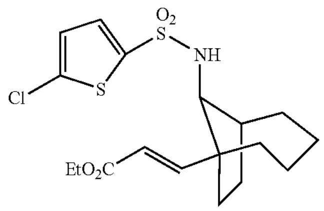

Potassium tert-butoxide (1.0M in THF, 7.0 ml) was added to a solution of triethyl phosphonoacetate (1.57 g) in dry THF (30 ml). The reaction was stirred at room temperature for 30 min then a solution of the aldehyde from Example 10 (0.49 g) in dry THF (20 ml) was added. The reaction was stirred for 3 h then quenched with 2N HCl and concentrated in vacuo. The residue was extracted with EtOAc, washed with brine, dried over $MgSO_4$ and concentrated in vacuo. Purification by column chromatography (silica, 10–15% EtOAc in hexane) gave ethyl (2E)-3-((1R/S,6S/R,9S/R)-9-{[(5-chlorothien-2-yl)sulfonyl]amino}bicyclo[4.2.1]non-1-yl)prop-2-enoate as a white solid (0.56 g, 95%).

(360 MHz $^1$H, $CDCl_3$) 1.29 (3H, t, J=7.1), 1.43–1.86 (12H, m), 2.00–2.07 (1H, m), 2.48–2.54 (1H, m), 3.58 (1H, dd, J=8.2, 8.2), 4.17 (2H, q, J=7.1); 4.78 (1H, d, J=8.2), 5.64

(1H, d, J=16.0), 6.73 (1H, d, J=16.0), 6.87 (1H, d, J=4.0), 7.38 (1H, d, J=4.0); ($^{13}$C, $CDCl_3$) 16.1, 25.6, 27.6, 30.9, 31.8, 36.0, 40.7, 51.1, 62.2, 65.9, 120.8, 128.5, 133.6, 139.1, 140.9, 157.0, 168.3. MS (ES+): [M+Na]+ 440, [M−OEt]+ 372.

EXAMPLE 17

Methyl N-((1S/R,6S/R,9S/R)-9-{[(5-chlorothien-2-yl)sulfonyl]amino}bicyclo[4.2.1]non-1-yl)glycinate

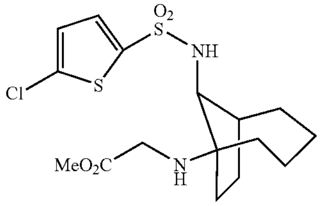

Hydrogen chloride gas was bubbled through a solution of the BOC-protected amine from Example 11 (88 mg) in ether (30 ml) at 0° C. for 1 h. The reaction was concentrated in vacuo and triturated with ether to give the amine as the hydrochloride salt (73 mg, 97%). A suspension of the amine hydrochloride and potassium carbonate (54 mg) in acetone (10 ml) was stirred for 10 min then methyl bromoacetate (30 mg) was added. The reaction was stirred for 16 h then concentrated in vacuo. Water was added and the reaction extracted with EtOAc, dried over $MgSO_4$ and concentrated in vacuo. The product was purified by column chromatography (silica, 40% EtOAc in hexane) to give methyl N-((1S/R,6S/R,9S/R)-9-{[(5-chlorothien-2-yl)sulfonyl]amino}bicyclo[4.2.1]non-1-yl)glycinate as a white solid (49 mg, 61%).

(400 MHz $^1$H, $CDCl_3$) 1.43–1.81 (11H, m), 1.99 (1H, brm), 2.37 (1H, brm), 3.12 (1H, d, J=16.9), 3.29 (1H, d, J=16.9), 3.42 (1H, dd, J=6.7, 6.7), 3.72 (3H, s), 4.74 (1H, m), 6.93 (1H, d, J=4.0), 7.45 (1H, d, J=4.0); ($^{13}$C, $CDCl_3$) 23.2, 25.0, 27.7, 30.1, 31.5, 36.4, 37.5, 44.4, 52.0, 62.8, 64.7, 126.7, 132.0, 137.4, 138.7 172.8. MS (ES+): MH+ 407.

EXAMPLE 18

5-Chloro-N-[(1S/R,6S/R,9S/R)-1-(4,5-dihydro-1H-imidazol-2-yl)bicyclo[4.2.1]non-9-yl]thiophene-2-sulfonamide

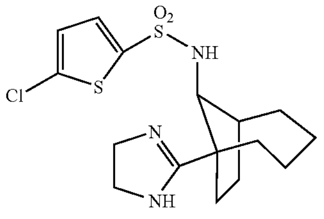

Hydrogen chloride gas was bubbled through a solution of the nitrile from Example 14 (0.120 g) in ether (2 ml), DCM (2 ml) and MeOH (1 ml) at 0° C. for 45 min. The reaction was stirred at room temperature for 16 h then concentrated in vacuo and triturated with ether. The resulting crude ethyl (1S/R,6S/R,9S/R)-9-{[(5-chlorothien-2-yl)sulfonyl]amino}bicyclo[4.2.1]nonane-1-carboximidoate and ethylenediamine (1 ml) in EtOH were stirred for 5 h then concentrated in vacuo. 4N NaOH was added and the reaction extracted with DCM, dried over $MgSO_4$ and concentrated in vacuo. Purification by column chromatography (silica, 2% ammonia solution, 10% MeOH in DCM) gave 5-chloro-N-[(1S/R,6S/R,9S/R)-1-(4,5-dihydro-1H-imidazol-2-yl)bicyclo[4.2.1]non-9-yl]thiophene-2-sulfonamide as a white solid (53 mg, 39%).

(400 MHz $^1$H, $d_4$-MeOH) 1.52–2.06 (12H, m), 2.40 (1H, m), 3.60 (4H, s), 3.74 (1H, d, J=11.7), 7.01 (1H, d, J=3.9), 7.34 (1H, d, J=3.9). MS (ES+): MH+ 388.

EXAMPLE 19

Ethyl(1R/S,6R/S,9S/R)-9-{[(5-chlorothien-2-yl)sulfonyl]amino}bicyclo[4.2.1]non-3-ene-1-carboxylate

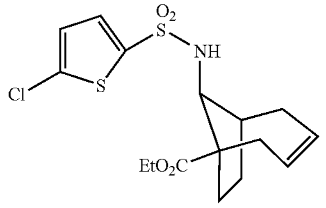

(1) To a solution of ethyl (1R/S,6R/S)-9-oxobicyclo[4.2.1]non-3-ene-1-carboxylate (146 mg; *J. Am. Chem. Soc.,* 1969, 2812) in ethanol (2 ml) were added hydroxylamine hydrochloride (146 mg) and sodium acetate (173 mg), and the mixture heated to reflux for 2.5 hrs., then concentrated in vacuo, treated with water (5 ml) and extracted with DCM (3×20 ml). Drying and concentration gave ethyl (1R/S,6R/S,9E/Z)-9-(hydroxyimino)bicyclo[4.2.1]non-3-ene-1-carboxylate as a mixture of isomers (3:2) (145 mg, 93%).

(2) To a solution of the oxime from Step (1) (145 mg) in MeOH (5 ml) at −30° C. under nitrogen were added methyl orange indicator (0.1% aq, 1 drop) and $NaCNBH_3$ (82 mg). Sufficient HCl (5M) was added to avail the solution of a pale pink colour and the reaction stirred for 4 hrs, adding HCl periodically to maintain a pink hue. The reaction was allowed to warm to room temperature before adding ice-chilled NaOH (2M, 3 ml) and extracting with EtOAc (3×5 ml). Drying and concentration gave ethyl (1R/S,6R/S,9S/R)-9-(hydroxyamino)bicyclo[4.2.1]non-3-ene-1-carboxylate as a pale yellow oil (85 mg, 58%).

(3) To the hydroxyamine (85 mg) in acetic acid at room temperature was added zinc dust (200 mg) and the mixture stirred for 1 hr., filtered through Celite™ and washed with MeOH/DCM. The filtrate was concentrated, partitioned between saturated sodium bicarbonate (5 ml) and DCM (5 ml). Drying and concentration of the organic phase gave ethyl (1R/S,6R/S,9S/R)-9-aminobicyclo[4.2.1]non-3-ene-1-carboxylate as a gum (55 mg, 77%).

(4) A mixture of the amine from Step (3) (118 mg), 5-chloro-2-thiophenesulfonyl chloride (148 mg) and N-methylmorpholine (95 μl) in DCM (2 ml) was stirred for 16 hrs under nitrogen. After addition of water, extraction with DCM (3×10 ml), drying and concentration, column chromatography on silica eluting with 10% EtOAc/hexane gave ethyl (1R/S,6R/S,9S/R)-9-{[(5-chlorothien-2-yl)sulfonyl]amino}bicyclo[4.2.1]non-3-ene-1-carboxylate as a white powder (96 mg, 44%).

(360 MHz $^1$H, $CDCl_3$) 1.22 (3H, t, J=7.1), 1.49 (1H, m), 1.71 (1H, m), 1.94 (1H, m), 2.05–2.30 (3H, m), 2.49 (2H, m), 4.05 (2H, m), 4.35 (1H, dd, J=4.5, 9.9), 4.77 (1H, d, J=9.9), 5.51 (2H, m), 6.90 (1H, d, J=4), 7.40 (1H, d, J=4); MS (ES+): MH+ 390.

EXAMPLE 20

5-Chloro-N-[(1R/S,6R/S,9S/R)-1-hydroxymethyl)bicyclo[4.2.1]non-3-en-9-yl]thiophene-2-sulfonamide

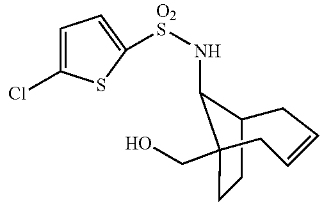

To the product from Example 19 (45 mg) in THF (2 ml) at 0° C. under nitrogen was added $LiAlH_4$ (127 μl) dropwise. After warming to room temperature and stirring for 1.5 hrs., standard work-up using water/NaOH/water followed by extraction with EtOAc, then column chromatography on silica eluting with 30% EtOAc/hexane, gave 5-chloro-N-[(1R/S,6R/S,9S/R)-1-(hydroxymethyl)bicyclo[4.2.1]non-3-en-9-yl]thiophene-2-sulfonamide as a white solid (30 mg, 63%).

(360 MHz $^1$H, $CDCl_3$) 1.43 (2H, m), 1.78 (2H, m), 1.95–2.13 (4H, m), 2.23 (1H, m), 3.39 (1H, d, J=11.3), 3.48 (1H, d, J=11.2), 3.84 (1H, dd, J=7.7, 10.4), 4.79 (1H, d, J=10.3), 5.51 (2H, m), 6.92 (1H, d, J=4), 7.42 (1H, d, J=3.6); ($^{13}$C, $CDCl_3$) 28.6, 31.6, 33.7, 37.0, 39.7, 49.9, 61.7, 69.5, 128.51, 128.57, 128.71, 133.3, 139.1, 141.8; MS (ES+): MH+ 348.

EXAMPLE 21

(2E)-3-((1R/S,6S/R,9S/R)-9-{[(5-Chlorothien-2-yl)sulfonyl]amino}bicyclo[4.2.1]non-1-yl)prop-2-enoic acid

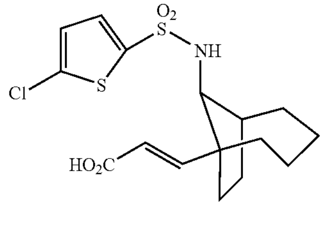

A solution of the ethyl ester from Example 16 (100 mg) in THF (20 ml) and 4N NaOH (50 ml) was heated at 60° C. for 16 h. The reaction was concentrated in vacuo, acidified with 2N HCl, extracted with DCM, dried over $MgSO_4$ and concentrated in vacuo. Trituration with hexane gave (2E)-3-((1R/S,6S/R,9S/R)-9-{[(5-chlorothien-2-yl)sulfonyl]amino}bicyclo[4.2.1]non-1-yl)prop-2-enoic acid as a white solid (86 mg, 92%).

(400 MHz $^1$H, $d_6$-DMSO) 1.32–1.84 (11H, m), 2.00 (1H, m), 2.37 (1H, m), 3.42 (1H, m), 5.53 (1H, d, J=15.9), 6.61 (1H, d, J=15.9), 7.13 (1H, d, J=4.0), 7.46 (1H, d, J=4.0), 7.68 (1H, d; J=6.2), 12.03 (1H, s); MS (ES+): (M+Na)+ 412.

EXAMPLE 22

(2E)-3-((1R/S,6S/R,9S/R)-9-{[(5-Chlorothien-2-yl)sulfonyl]amino}bicyclo[4.2.1]non-1-yl)prop-2-enamide

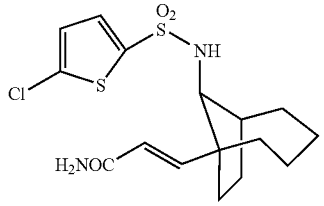

A solution of the acid from Example 21 (56 mg) in THF (20 ml) was cooled to 0° C. and oxalyl chloride (0.05 ml) was added. The reaction was stirred for 1 h at room temperature then at 60° C. for 1 h. The reaction was concentrated in vacuo, the residue dissolved in THF (5 ml) and cooled to 0° C. Ammonia gas was bubbled through the solution for 10 min, then methanol (5 ml) was added and the reaction concentrated in vacuo. The product was purified by column chromatography (silica, 5% MeOH in DCM) to give (2E)-3-((1R/S,6S/R,9S/R)-9-{[(5-chlorothien-2-yl)sulfonyl]amino}bicyclo[4.2.1]non-1-yl)prop-2-enamide as a white solid (37 mg, 66%).

(360 MHz $^1$H, $d_6$-DMSO) 1.36–1.83 (11H, m), 1.97 (1H, brm), 2.35 (1H, brm), 3.39 (1H, brm), 5.73 (1H, d, J=15.7), 6.47 (1H, d, J=15.7), 6.82 (1H, s), 7.12 (1H, d, J=4.0), 7.18 (1H, s), 7.44 (1H, d, J=4.0), 7.66 (1H, s).

EXAMPLE 23

5-Chloro-N-{(1S/R,6S/R,9S/R)-1-[(E)-(hydroxyimino)methyl]bicyclo[4.2.1]non-9-yl}thiophene-2-sulfonamide

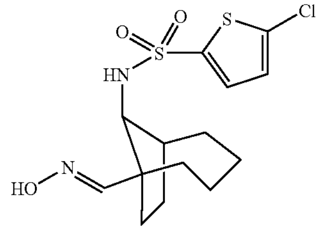

A mixture of the aldehyde from Example 10 (52 mg), hydroxylamine hydrochloride (31 mg) and sodium acetate trihydrate (61 mg) in ethanol (10 ml) was heated under reflux for 16 h. 2N HCl (10 ml) was added and the reaction was extracted with EtOAc, washed with brine, dried over $MgSO_4$ and concentrated in vacuo. The product was purified by column chromatography (silica, 20% EtOAc in hexane) to give 5-chloro-N-{(1S/R,6S/R,9S/R)-1-[(E)-(hydroxyimino)methyl]bicyclo[4.2.1]non-9-yl}thiophene-2-sulfonamide as a white solid (38 mg, 70%).

(400 MHz $^{1}H$, $CDCl_3$) 1.47–1.88 (11H, m), 2.04 (1H, brm), 2.50 (1H, brm), 3.57 (1H, t, J=7.2), 4.89 (1H, d, J=7.2), 6.91 (1H, d, J=4.0), 7.17 (1H, s), 7.20 (1H, brs), 7.39 (1H, d, J=4.0); ($^{13}C$, $CDCl_3$) 25.6, 27.4, 30.8, 32.0, 34.5, 35.7, 40.3, 50.9, 64.8, 128.5, 133.7, 139.2, 140.6, 159.1.

EXAMPLE 24

3-((1R/S,6S/R,9S/R)-9-{[(5-Chlorothien-2-yl)sulfonyl]amino}bicyclo[4.2.1]non-1-yl)propanamide

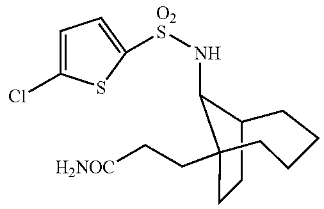

A mixture of the prop-2-enamide from Example 22 (38 mg) and catalyst (5% Rh on carbon) in EtOH (15 ml) and EtOAc (5 ml) was hydrogenated at 40 psi for 16 h. The reaction was filtered through Celite™ and concentrated in vacuo. The product was purified by column chromatography (silica, 2% MeOH in DCM) to give 3-((1R/S,6S/R,9S/R)-9-{[(5-chlorothien-2-yl)sulfonyl]amino}bicyclo[4.2.1]non-1-yl)propanamide as a white solid (9 mg, 24%).

(400 MHz $^{1}H$, $d_6$-DMSO) 1.14–1.65 (13H, m), 1.79 (2H, m), 1.94 (1H, m), 2.25 (1H, m), 3.15 (1H, d, J=7.4), 6.60 (1H, s), 7.10 (1H, s), 7.20 (1H, d, J=4.0), 7.48 (1H, s), 7.50 (1H, d, J=4.0).

EXAMPLE 25

5-Chloro-N-{(1R/S,6S/R,9S/R)-1-[(1E)-3-hydroxyprop-1-enyl]bicyclo[4.2.1]non-9-yl}thiophene-2-sulfonamide

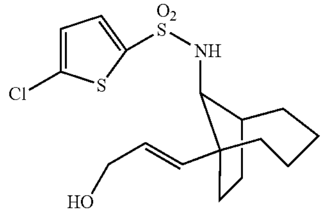

Diisobutylaluminium hydride (6.0 ml, 1.0M in hexanes) was added dropwise to a solution of the ethyl prop-2-enoate ester from Example 16 (0.85 g) in THF (20 ml) and ether (60 ml) at −78° C. The reaction was stirred at −78° C. for 1 h then at room temperature for 16 h. The reaction was quenched with saturated $NH_4Cl$ solution (60 ml), extracted with EtOAc, washed with brine, dried over $MgSO_4$ and concentrated in vacuo. The product was purified by column chromatography (silica, 10–30% EtOAc in hexane) to give 5-chloro-N-{(1R/S,6S/R,9S/R)-1-[(1E)-3-hydroxyprop-1-enyl]bicyclo[4.2.1]non-9-yl}thiophene-2-sulfonamide as a white solid (0.31 g, 41%).

(360 MHz $^{1}H$, $CDCl_3$) 1.36–1.86 (12H, m), 2.03 (1H, brm), 2.42 (1H, brm), 3.45 (1H, m), 3.99 (2H, d, J=4.8), 4.63 (1H, d, J=8.0), 5.54 (2H, m), 6.91 (1H, d, J=4.0), 7.39 (1H, d, J=4.0).

EXAMPLE 26

N-{(1S/R,6S/R,9S/R)-1-[(Benzyloxy)methyl]bicyclo[4.2.1]non-9-yl}-5-chlorothiophene-2-sulfonamide

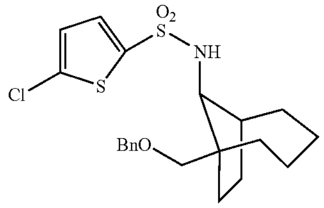

To a solution of the alcohol from Example 9 (35 mg) in THF (2 ml) at 0° C. was added sodium hydride (9 mg, 60% dispersion in mineral oil). The reaction was stirred at 0° C. for 0.5 h then benzyl bromide (13 μl) was added. The reaction was stirred at room temperature for 4 h then at 50° C. for 16 h. The reaction was quenched with water (5 ml), extracted with EtOAc, washed with brine, dried over $MgSO_4$ and concentrated in vacuo. The product was purified by column chromatography (silica, 10% EtOAc in hexane) to give N-{(1S/R,6S/R,9S/R)-1-[(benzyloxy)methyl]bicyclo[4.2.1]non-9-yl}-5-chlorothiophene-2-sulfonamide as a white solid (37 mg, 84%).

(360 MHz $^{1}H$, $CDCl_3$) 0.87 (2H, m), 1.22–1.68 (8H, m), 1.85 (2H, m), 2.46 (1H, m), 3.08 (1H, d, J=8.7), 3.20 (1H, d, J=8.7), 3.46 (1H, dd, J=5.1, 6.9), 4.36 (2H, m), 5.11 (1H, d, J=5.1), 6.83 (1H, d, J=4.0), 7.24–7.38 (6H, m).

EXAMPLE 27

5-Chloro-N-((1S/R,6S,R,9S,R)-1-{[(4-methoxybenzyl)oxy]methyl}bicyclo[4.2.1]non-9-yl)thiophene-2-sulfonamide

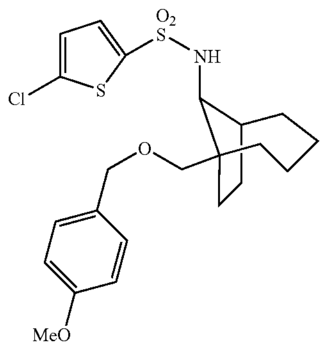

Prepared by the procedure of Example 26, using 4-methoxybenzyl bromide.

(360 MHz $^{1}H$, $CDCl_3$) 0.86 (1H, m), 1.26–1.68 (9H, m), 1.85 (2H, m), 2.45 (1H, m), 3.05 (1H, d, J=8.7), 3.17 (1H, d, J=8.7), 3.43 (1H, dd, J=4.8, 7.0), 3.82 (3H, s), 4.30 (2H, s), 5.15 (1H, d, J=4.8), 6.87 (3H, m), 7.17 (2H, m), 7.29 (1H, d, J=4.0). MS (ES+): (M+Na)+ 492.

EXAMPLE 28

Methyl(1S/R,5S/R,8S/R)-8-{[(5-chlorothien-2-yl)sulfonyl]amino}bicyclo[3.2.1]octane-1-carboxylate

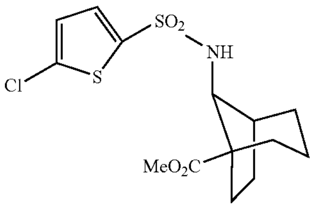

(1) A mixture of methyl (1R,S,5R,S)-8-oxobicyclo[3.2.1]oct-2-ene-1-carboxylate (60 mg, *J. Org. Chem.*, 1996, 61, 7832) and 5% Pd on carbon in MeOH (20 ml) was hydrogenated at 40 psi for 5 h. The reaction was filtered through Celite™ and concentrated in vacuo. Methyl(1S,5S)-8-oxobicyclo[3.2.1]octane-1-carboxylate was purified by column chromatography (silica, 10% EtOAc in hexane) to give an oily solid (61 mg, 100%).

(2) To a solution of methyl (1S,5S)-8-oxobicyclo[3.2.1]octane-1-carboxylate (0.45 g), triethylamine (1.0 ml) and 5-chlorothiophene-2-sulfonamide (0.98 g) in dry DCM (15 ml) at 0° C. was added $TiCl_4$ (1.0M in DCM, 3.7 ml). The reaction was stirred at 0° C. for 4 h then quenched with water (15 ml). The reaction was diluted with 2N HCl (10 ml), extracted with DCM, washed with brine, dried over $MgSO_4$ and concentrated in vacuo. Crude methyl (1S/R,5S/R,8E/Z)-8-{[(5-chlorothien-2-yl)sulfonyl]imino}bicyclo[3.2.1]octane-1-carboxylate was suspended in hexane (200 ml) and heated under reflux for 5 min then filtered through Celite™ and concentrated in vacuo.

(3) A solution of the imine from Step 2 in MeOH (20 ml) was cooled to 0° C. and $NaBH_4$ (0.1 g) was added portionwise. The reaction was stirred at room temperature for 30 min then concentrated in vacuo. After addition of 2N HCl (15 ml), extraction with EtOAc, washing with brine, drying over $MgSO_4$ and concentration in vacuo, the product was purified by column chromatography (silica, 15% EtOAc in hexane) to give methyl (1S/R,5S/R,8S/R)-8-{[(5-chlorothien-2-yl)sulfonyl]amino}bicyclo[3.2.1]octane-1-carboxylate as a white solid (0.68 g, 76%).

(360 MHz $^1H$, $CDCl_3$) 1.27–1.31 (1H, m), 1.54–1.61 (4H, m), 1.72–1.87 (4H, m), 1.98–2.02 (1H, m), 2.38–2.39 (1H, m), 3.45 (1H, t, J=4.7), 3.58 (3H, s), 5.30 (1H, d, J=4.7), 6.93 (1H, d, J=4.0), 7.41 (1H, d, J=4.0); ($^{13}C$, $CDCl_3$) 19.2, 25.6, 26.8, 29.6, 31.8, 38.9, 52.2, 53.9, 61.2, 128.5, 133.6, 139.1, 140.5, 177.9.

EXAMPLE 29

5-Chloro-N-[(1S/R,5S/R,8S/R)-1-(hydroxymethyl)bicyclo[3.2.1]oct-8-yl]thiophene-2-sulfonamide

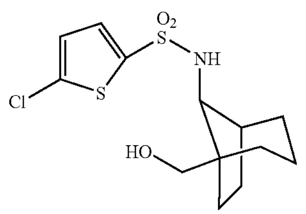

To a solution of the methyl ester from Example 28 (200 mg) in dry THF (5 ml) at 0° C. was added lithium aluminium hydride (1.0M in ether, 0.6 ml). The reaction was stirred at 0° C. for 1 h then quenched with water (5 ml), extracted with EtOAc, washed with brine, dried over $MgSO_4$ and concentrated in vacuo. The product was purified by column chromatography (silica, 20% EtOAc in hexane) to give 5-chloro-N-[(1S/R,5S/R,8S/R)-1-(hydroxymethyl)bicyclo[3.2.1]oct-8-yl]thiophene-2-sulfonamide as a white solid (158 mg, 85%).

(360 MHz $^1H$, $CDCl_3$) 1.08 (1H, m), 1.34–1.76 (9H, m), 2.03 (1H, m), 2.10 (1H, s), 3.27 (1H, d, J=11.5), 3.31 (1H, m), 3.53 (1H, d, J=11.5), 5.20 (1H, d, J=7.6), 6.92 (1H, d, J=4.0), 7.41 (1H, d, J=4.0).

EXAMPLE 30

5-Chloro-N-[(1S/R,5S/R,8S/R)-1-(methoxymethyl)bicyclo[3.2.1]oct-8-yl]thiophene-2-sulfonamide

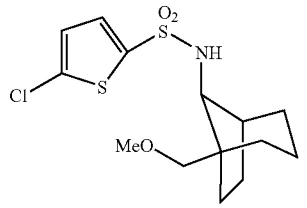

To a solution of the alcohol from Example 29 (50 mg) in THF (2 ml) at 0° C. was added sodium hydride (15 mg, 60% dispersion in mineral oil). The reaction was stirred at 0° C. for 20 min then methyl iodide (10 μl) was added. The reaction was stirred at room temperature for 16 h. The reaction was quenched with water (5 ml), extracted with EtOAc, washed with brine, dried over $MgSO_4$ and concentrated in vacuo. The product was purified by column chromatography (silica, 10% EtOAc in hexane) to give 5-chloro-N-[(1S/R,5S/R,8S/R)-1-(methoxymethyl)bicyclo[3.2.1]oct-8-yl]thiophene-2-sulfonamide as a white solid (39 mg, 75%).

(360 MHz $^1H$, $CDCl_3$) 1.11 (1H, m), 1.22–1.86 (9H, m), 2.33 (1H, m), 3.04 (1H, d, J=9.0), 3.06 (1H, m), 3.17 (1H, d, J=9.0), 3.21 (3H, s), 5.54 (1H, s), 6.92 (1H, d, J=4.0), 7.38 (1H, d, J=4.0).

EXAMPLE 31

5-Chloro-N-{(1S/R,5S/R,8S/R)-1-[(2-morpholin-4-ylethoxy)methyl]bicyclo[3.2.1]oct-8-yl}thiophene-2-sulfonamide hydrochloride.

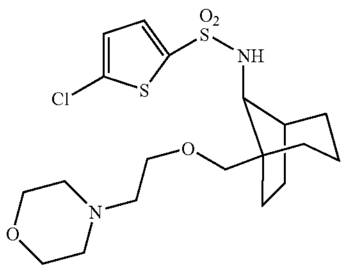

To a solution of the alcohol from Example 29 (84 mg) in DMF (2 ml) at 0° C. was added sodium hydride (22 mg, 60% dispersion in mineral oil). The reaction was stirred at 0° C.

for 30 min then 4-(2-chloroethyl)morpholine (56 mg) was added. The reaction was stirred at room temperature for 1 h then heated at 80° C. for 16 h. The reaction was cooled, quenched with water (10 ml), extracted with EtOAc, washed with water (2×10 ml) and brine (10 ml), dried over $MgSO_4$ and concentrated in vacuo. The product was purified by column chromatography (silica, 2% MeOH in DCM). The amine was dissolved in ether and HCl gas bubbled through the solution to give 5-chloro-N-{(1S/R,5S/R,8S/R)-1-[(2-morpholin-4-ylethoxy)methyl]bicyclo[3.2.1]oct-8-yl}thiophene-2-sulfonamide hydrochloride as a yellow solid (10 mg, 8%).

(360 MHz $^1$H, $d_6$-DMSO) 0.84 (1H, m), 1.07–1.77 (10H, m), 3.12 (4H, m), 3.26 (3H, m), 3.64 (4H, m), 3.76 (2H, m), 3.95 (2H, m), 7.25 (1H, d, J=3.9), 7.49 (1H, d, J=3.9), 7.93 (1H, d, J=8.6), 10.53 (1H, s).

EXAMPLE 32

((1S,5S,8S)-8-{[(5-Chlorothien-2-yl)sulfonyl]amino}bicyclo[3.2.1]oct-1-yl)methyl 3-(1H-imidazol-1-yl)propylcarbamate hydrochloride

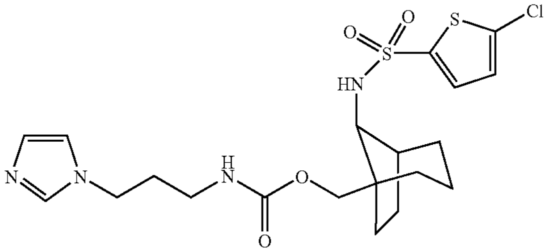

(1) To a solution of the alcohol from Example 29 (0.470 g) in THF (7 ml) and MeCN (1 ml) was added pyridine (0.11 ml) followed by 4-nitrophenyl chloroformate (0.310 g). The reaction was stirred at room temperature for 16 h. The reaction concentrated in vacuo, diluted with ether, washed with water and brine (10 ml), dried over $MgSO_4$ and concentrated in vacuo. ((1S/R,5S/R,8S/R)-8-{[(5-Chlorothien-2-yl)sulfonyl]amino}bicyclo[3.2.1]oct-1-yl)methyl 4-nitrophenyl carbonate was purified by column chromatography (silica, 5–25% EtOAc in hexane) to give a yellow oil (0.509 g, 73%).

(2) To a solution of the carbonate from Step (1) (51 mg) in MeOH (2 ml) was added 1-(3-aminopropyl)imidazole (25 mg). The reaction was stirred at room temperature for 30 min. The reaction was concentrated in vacuo, diluted with DCM, washed with 10% sodium carbonate solution, dried over $MgSO_4$ and concentrated in vacuo. The product was purified by column chromatography (silica, 2–5% MeOH in DCM) to give a white solid (24 mg, 49%). The free base was dissolved in ether and hydrogen chloride gas was bubbled through the solution to give ((1S/R,5S/R,8S/R)-8-{[(5-chlorothien-2-yl)sulfonyl]amino}bicyclo[3.2.1]oct-1-yl)methyl 3-(1H-imidazol-1-yl)propylcarbamate hydrochloride as a white solid.

(400 MHz $^1$H, $\delta_6$-DMSO) 1.12 (2H, m), 1.29–1.76 (8H, m), 1.95 (3H, m), 2.98 (2H, m), 3.28 (1H, m), 3.66 (2H, m), 4.20 (2H, m), 6.89 (1H, s), 7.15 (1H, d, J=4.0), 7.44 (1H, d, J=4.0), 7.62 (1H, s), 7.71 (1H, s), 7.80 (1H, d, J=8.2), 9.03 (1H, s).

EXAMPLE 33

((1S/R,5S/R,8S/R)-8-{[(5-Chlorothien-2-yl)sulfonyl]amino}bicyclo[3.2.1]oct-1-yl)methyl 3-morpholin-4-ylpropylcarbamate hydrochloride.

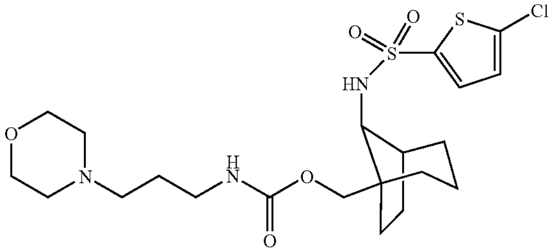

Prepared by procedure of Example 32, using 4-(3-aminopropyl)morpholine in Step (2).

(400 MHz $^1$H, $d_6$-DMSO) 1.11–1.90 (13H, m), 3.05 (6H, m), 3.29 (3H, m), 3.63 (1H, d, J=10.8), 3.69 (1H, d, J=10.8), 3.82 (2H, m), 3.91 (2H, m), 6.87 (1H, s), 7.17 (1H, d, J=4.0), 7.45 (1H, d, J=4.0), 7.80 (1H, d, J=8.0), 10.83 (1H, s).

EXAMPLE 34

((1S/R,5S/R,8S/R)-8-{[(5-chlorothien-2-yl)sulfonyl]amino}bicyclo[3.2.1]oct-1-yl)methyl butylcarbamate

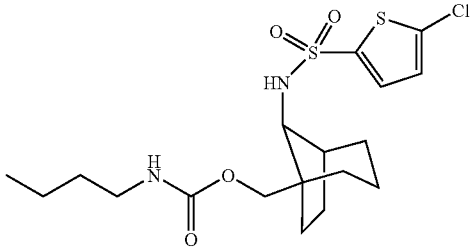

Prepared by procedure of Example 32, using n-butylamine in Step (2).

(400 MHz $^1$H, $d_6$-DMSO) 0.86 (3H, t, J=7.2), 1.10–1.77 (14H, m), 1.94 (1H, s), 2.93 (2H, m), 3.25 (1H, m), 3.59 (1H, d, J=10.8), 3.68 (1H, d, J=10.8), 6.60 (1H, s), 7.14 (1H, d, J=3.9), 7.44 (1H, d, J=3.9), 7.74 (1H, d, J=7.4).

EXAMPLE 35

((1S/R,5S/R,8S/R)-8-{[(5-Chlorothien-2-yl)sulfonyl]amino}bicyclo[3.2.1]oct-1-yl)methyl propylcarbamate

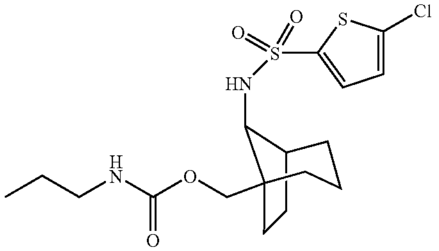

Prepared by procedure of Example 32, using n-propylamine in Step (2).

(400 MHz $^1$H, $d_6$-DMSO) 0.83 (3H, t, J=7.4), 1.13 (2H, m), 1.31–1.74 (10H, m), 1.94 (1H, m), 2.90 (2H, dt, J=6.3, 6.3), 3.26 (1H, m), 3.59 (1H, d, J=10.6), 3.68 (1H, d, J=10.6), 6.62 (1H, brs), 7.14 (1H, d, J=4.0), 7.44 (1H, d, J=4.0), 7.74 (1H, d, J=7.3).

EXAMPLE 36

((1S/R,5S/R,8S/R)-8-{[(5-Chlorothien-2-yl)sulfonyl] amino}bicyclo[3.2.1]oct-1-yl)methyl 2-pyridin-2-ylethylcarbamate

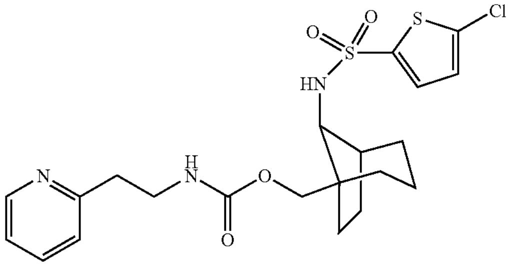

Prepared by procedure of Example 32, using 2-(2-aminoethyl)pyridine in Step (2).

(400 MHz $^1$H, $d_6$-DMSO) 1.09 (2H, m), 1.24–1.72 (8H, m), 1.89 (1H, m), 2.49 (2H, m), 3.25 (1H, m), 3.43 (2H, m), 3.57 (1H, d, J=10.8), 3.65 (1H, d, J=10.8), 6.93 (1H, m), 7.16 (1H, d, J=3.1), 7.44 (1H, d, J=3.1), 7.76 (3H, m), 8.32 (1H, t, J=7.5), 8.71 (1H, d, J=4.8).

EXAMPLE 37

((1S/R,5S/R,8S/R)-8-{[(5-Chlorothien-2-yl)sulfonyl] amino}bicyclo[3.2.1]oct-1-yl)methyl 2-(2-oxoimidazolidin-1-yl)ethylcarbamate

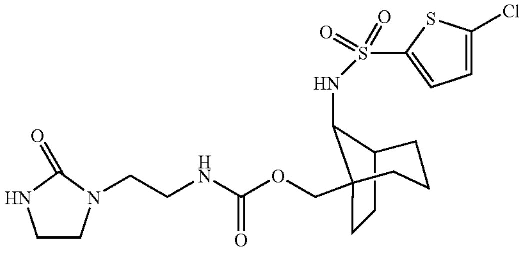

Prepared by procedure of Example 32, using 1-(2-aminoethyl)-2-oxoimidazolidine in Step (2).

(400 MHz $^1$H, $d_6$-DMSO) 1.11 (2H, m), 1.39–1.77 (8H, m), 1.92 (1H, m), 3.08 (4H, m), 3.22 (3H, m), 3.34 (2H, m), 3.60 (1H, d, J=10.8), 3.70 (1H, d, J=10.8), 6.06 (1H, s), 6.69 (1H, m), 7.16 (1H, d, J=3.9), 7.44 (1H, d, J=3.9), 7.76 (1H, d, J=7.4).

EXAMPLE 38

((1S/R,5S/R,8S/R)-8-{[(5-Chlorothien-2-yl)sulfonyl] amino}bicyclo[3.2.1]oct-1-yl)methyl 2-morpholin-4-ylethylcarbamate hydrochloride.

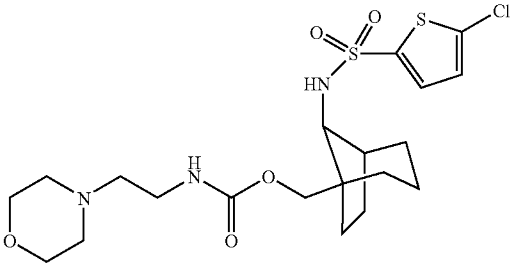

Prepared by procedure of Example 32, using 4-(2-aminoethyl)morpholine in Step (2).

(400 MHz $^1$H, $d_6$-DMSO) 1.12 (2H, m), 1.36–1.76 (8H, m), 1.88 (1H, m), 3.14 (4H, m), 3.28 (1H, m), 3.41 (4H, m), 3.66 (1H, d, J=10.7), 3.72 (1H, d, J=10.7), 3.90 (4H, m), 7.11 (11, s), 7.17 (1H, d, J=3.9), 7.47 (1H, d, J=3.9), 7.81 (1H, d, J=8.0), 11.28 (1H, s).

EXAMPLE 39

((1S/R,5S/R,8S/R)-8-{[(5-Chlorothien-2-yl)sulfonyl] amino}bicyclo[3.2.1]oct-1-yl)methyl 3-(2-oxopyrrolidin-1-yl)propylcarbamate

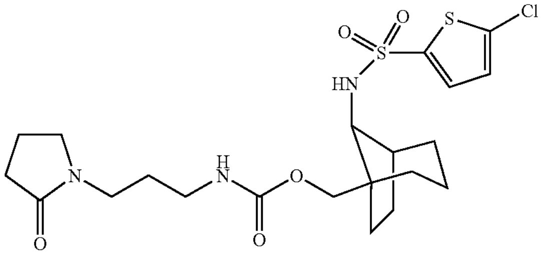

Prepared by procedure of Example 32, using 1-(3-aminopropyl)-2-oxopyrrolidine in Step (2).

(400 MHz $^1$H, $d_6$-DMSO) 1.12 (2H, m), 1.31–1.74 (11H, m), 1.91 (2H, m), 2.19 (2H, m), 2.93 (2H, m), 3.16 (2H, m), 3.26 (1H, m), 3.30 (2H, m), 3.60 (1H, d, J=10.5), 3.68 (1H, d, J=10.5), 6.63 (1H, s), 7.15 (1H, d, J=2.7), 7.44 (1H, d, J=2.7), 7.76 (1H, d, J=6.5).

EXAMPLE 40

((1S/R,6S/R,9S/R)-9-{[(5-Chlorothien-2-yl)sulfonyl] amino}bicyclo[4.2.1]non-1-yl)methyl 2-(2-oxoimidazolidin-1-yl)ethylcarbamate

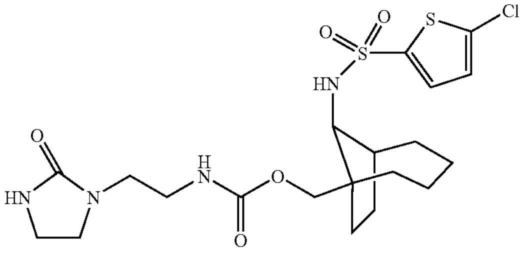

Prepared by procedure of Example 32, using the alcohol from Example 9 in Step (1) and 1-(2-aminoethyl)-2-oxoimidazolidine in Step (2).

(360 MHz $^1$H, $d_6$-DMSO) 1.25–1.78 (12H, m), 2.33 (1H, m), 3.09 (4H, m), 3.22 (2H, m), 3.34 (2H, m), 3.44 (1H, m), 3.51 (1H, d, J=10.3), 3.65 (1H, d, J=10.3), 6.04 (1H, s), 6.65 (1H, m), 7.14 (1H, d, J=3.9), 7.21 (1H, s), 7.45 (1H, d, J=3.9).

EXAMPLE 41

((1S/R,6S/R,9S/R)-9-{[(5-Chlorothien-2-yl)sulfonyl]amino}bicyclo[4.2.1]non-1-yl)methyl 3-morpholin-4-ylpropylcarbamate hydrochloride.

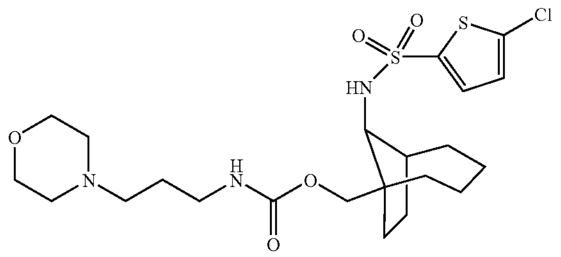

Prepared by procedure of Example 32, using the alcohol from Example 9 in Step (1) and 4-(3-aminopropyl)morpholine in Step (2).

(400 MHz $^1H$, $d_6$-DMSO) 1.24–1.88 (14H, m), 2.31 (1H, m), 3.04 (6H, m), 3.35 (2H, m), 3.46 (1H, m), 3.55 (1H, d, J=10.5), 3.65 (1H, d, J=10.5), 3.80 (2H, m), 3.93 (2H, m), 6.85 (1H, s), 7.16 (1H, d, J=4.0), 7.27 (1H, d, J=5.5), 7.47 (1H, d, J=4.0), 10.76 (1H, s).

EXAMPLE 42

((1S/R,6S/R,9S/R)-9-{[(5-Chlorothien-2-yl)sulfonyl]amino}bicyclo[4.2.1]non-1-yl)methyl morpholine-4-carboxylate

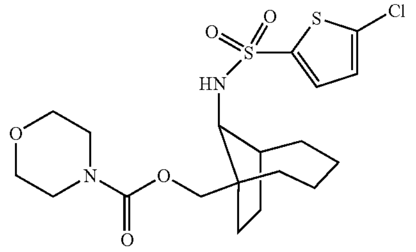

Prepared by procedure of Example 32, using the alcohol from Example 9 in Step (1) and morpholine in Step (2).

(400 MHz $^1H$, $\delta_6$-DMSO) 1.24–1.80 (12H, m), 2.33 (1H, m), 3.26 (4H, m), 3.42 (1H, m), 3.53 (4H, m), 3.62 (1H, d, J=10.7), 3.71 (1H, d, J=10.7), 7.17 (1H, d, J=4.0), 7.36 (1H, d, J=5.5), 7.46 (1H, d, J=4.0).

EXAMPLE 43

((1S/R,6S/R,9S/R)-9-{[(5-Chlorothien-2-yl)sulfonyl]amino}bicyclo[4.2.1]non-1-yl)methyl 4-(aminocarbonyl)piperidine-1-carboxylate

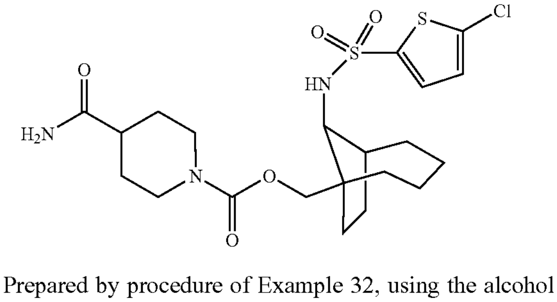

Prepared by procedure of Example 32, using the alcohol from Example 9 in Step (1) and 4-(aminocarbonyl)piperidine in Step (2).

(400 MHz $^1H$, $d_6$-DMSO) 1.24–1.76 (14H, m), 2.30 (2H, m), 2.74 (2H, m), 3.12 (1H, m), 3.42 (2H, m), 3.58 (1H, d, J=10.4), 3.71 (1H, d, J=10.4), 3.80 (2H, m), 6.57 (1H, s), 7.07 (1H, s), 7.15 (1H, m), 7.36 (1H, m), 7.46 (1H, m).

EXAMPLE 44

((1S/R,6S/R,9S/R)-9-{[(5-Chlorothien-2-yl)sulfonyl]amino}bicyclo[4.2.1]non-1-yl)methyl 3-(aminocarbonyl)piperidine-1-carboxylate

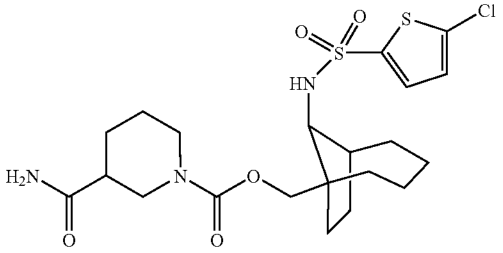

Prepared by procedure of Example 32, using the alcohol from Example 9 in Step (1) and 3-(aminocarbonyl)piperidine in Step (2).

(400 MHz $^1H$, $d_6$-DMSO) 1.28–1.87 (14H, m), 2.18 (1H, m), 2.32 (1H, m), 2.75 (2H, m), 3.40 (2H, m), 3.58 (1H, m), 3.71 (2H, m), 3.83 (2H, m), 6.61 (1H, s), 7.15 (2H, m), 7.35 (1H, m), 7.45 (1H, m).

EXAMPLE 45

[((1S/R,6S/R,9S/R)-9-{[(5-Chlorothien-2-yl)sulfonyl]amino}bicyclo[4.2.1]non-1-yl)methyl 4-(hydroxymethyl)piperidine-1-carboxylate

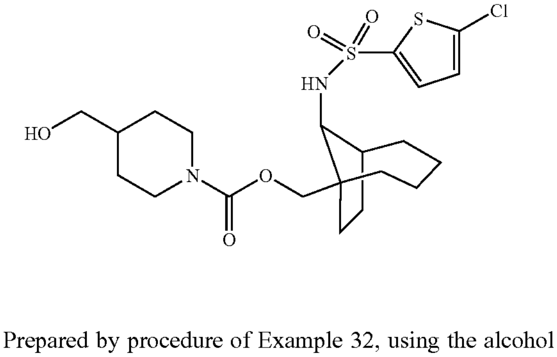

Prepared by procedure of Example 32, using the alcohol from Example 9 in Step (1) and 4-(hydroxymethyl)piperidine in Step (2).

(360 MHz $^1H$, $d_6$-DMSO) 0.99 (2H, m), 1.16–1.86 (14H, m), 2.33 (1H, m), 2.72 (2H, m), 2.96 (3H, m), 3.37 (1H, m), 3.58 (1H, d, J=10.5), 3.71 (1H, d, J=10.5), 3.84 (2H, m), 4.21 (1H, s), 7.15 (1H, m), 7.31 (1H, m), 7.45 (1H, m).

EXAMPLE 46

((1S/R,6S/R,9S/R)-9-{[(5-Chlorothien-2-yl)sulfonyl]amino}bicyclo[4.2.1]non-1-yl)methyl 4-hydroxypiperidine-1-carboxylate

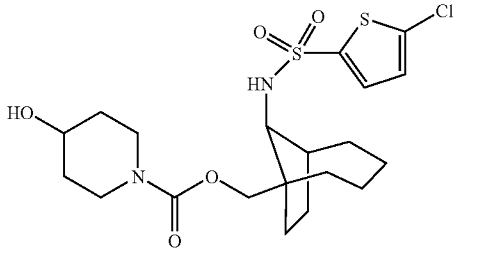

Prepared by procedure of Example 32, using the alcohol from Example 9 in Step (1) and 4-hydroxypiperidine in Step (2).

(400 MHz $^1H$, $d_6$-DMSO) 1.26–1.80 (14H, m), 2.33 (1H, m), 2.96 (2H, m), 3.42 (1H, m), 3.64 (6H, m), 3.70 (1H, d, J=10.7), 4.50 (1H, m), 7.15 (1H, d, J=4.0), 7.35 (1H, d, J=5.4), 7.45 (1H, d, J=4.0).

The invention claimed is:

1. A compound of formula I:

I

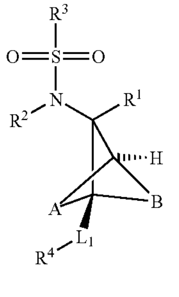

wherein:

A and B together with the carbon atoms bonded to -$L_1R^4$ and H complete a ring containing 5–10 carbon atoms, said ring bearing 0–2 substituents (in addition to -$L_1$-$R^4$) selected from:

=O, =S, =N—$OR^{11}$, =$CHR^{11}$, halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

and said ring optionally having fused thereto a further ring selected from $C_{6-10}$aryl, heteroaryl, heterocyclyl and $C_{5-10}$cycloalkyl, said further ring bearing 0–3 substituents independently selected from:

halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^1$ represents H, $C_{1-4}$alkyl or $C_{2-4}$alkenyl;

$R^2$ represents H, or $C_{2-6}$acyl which optionally bears a carboxylic acid or amino substituent;

$R^3$ represents $C_{1-10}$alkyl, $C_{3-10}$cycloalkyl, $C_{2-6}$alkenyl, $C_{2-6}$alkynyl, $C_{6-10}$aryl$C_{1-6}$alkyl, heteroaryl$C_{1-6}$alkyl, $C_{6-10}$aryl$C_{2-6}$alkenyl, heteroaryl$C_{2-6}$alkenyl, $C_{6-10}$aryl, heteroaryl, or heterocyclyl; wherein the alkyl, cycloalkyl, alkenyl and alkynyl groups represented by $R^3$ or forming part of a group represented by $R^3$ optionally bear a substituent selected from halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$NR^7CO_2R^8$ and —$NR^7SO_2R^8$; and the aryl, heteroaryl and heterocyclic groups represented by $R^3$ or forming part of a group represented by $R^3$ optionally bear up to 3 substituents independently selected from $R^8$, halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$NR^7CO_2R^8$ and —$NR^7SO_2R^8$;

$R^4$ represents H, halogen, Ar, heterocyclyl, CN, —$OR^9$, —$N(R^9)_2$, —$N(R^9)COR^{10}$, —$N(R^9)CO_2R^{10}$, —$OCOR^{10}$, —$COR^9$, —C(=$NOR^{11}$)$R^9$, —$CO_2R^9$, —$OCO_2R^{10}$, —$OSO_2R^9$, —$OSO_2N(R^9)_2$, —CON$(R^9)_2$, —$OCON(R^9)_2$, or —$CSN(R^9)_2$;

$L_1$ represents a covalent bond, $C_{1-6}$alkylene, $C_{2-6}$alkenylene, $C_{2-6}$alkynylene or $C_{1-4}$alkylene-W—$C_{1-4}$alkylene where W represents O, S, $SO_2$, NH, NH—CO—NH, O—CO—O, O—CO—NH or NH—CO—O, any of the alkylene groups optionally being substituted by halogen, CN, hydroxyl or $C_{1-4}$alkoxy; provided that if $R^4$ represents H, then $L_1$ does not represent a covalent bond;

$R^7$ represents H or $R^8$; or two $R^7$ groups together with a nitrogen atom to which they are mutually attached may complete a pyrrolidine, piperidine, piperazine or morpholine ring;

$R^8$ represents $C_{1-6}$alkyl, perfluoro$C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, Ar or —$C_{1-6}$alkylAr;

$R^9$ represents H or $R^{10}$; or two $R^9$ groups together with a nitrogen atom to which they are mutually attached may complete a 3–7 membered ring comprising up to 2 heteroatoms independently selected from N, O and S in addition to the nitrogen to which the $R^9$ groups are attached, said ring being optionally substituted by up to 3 substituents independently selected from halogen, oxo, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^{10}$ represents $C_{1-6}$alkyl, perfluoro$C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, $C_{6-10}$aryl, heteroaryl, heterocyclyl, $C_{6-10}$aryl$C_{1-6}$alkyl, heteroaryl$C_{1-6}$alkyl, $C_{6-10}$aryl$C_{2-6}$alkenyl or heteroaryl$C_{2-6}$alkenyl, wherein the alkyl, cycloalkyl, alkenyl and alkynyl groups optionally bear one substituent selected from halogen, $CF_3$, $NO_2$, CN, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$; and the aryl, heteroaryl and heterocyclic groups optionally bear up to 3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^{11}$ represents H or $R^{12}$;

$R^{12}$ represents $C_{1-6}$alkyl, hydroxy$C_{1-6}$alkyl, perfluoro$C_{1-6}$alkyl, $C_{2-6}$alkenyl, $C_{2-6}$alkynyl, Ar or —$C_{1-6}$alkylAr;

Ar is phenyl or heteroaryl either of which optionally bears up to 3 substituents independently selected from halogen, OH, $CF_3$, $NO_2$, CN, $C_{1-6}$alkyl and $C_{1-6}$alkoxy;

heterocyclyl at every occurrence thereof means a cyclic or polycyclic system of up to 10 ring atoms selected from C, N, O and S, wherein none of the constituent rings is aromatic and wherein at least one ring atom is other than C; and heteroaryl at every occurrence thereof means a cyclic or polycyclic system of up to 10 ring atoms selected from C, N, O and S, wherein at least one of the constituent rings is aromatic and wherein at least one ring atom of said aromatic ring is other than C;

with the proviso that if A represents 1,2-benzenediyl, and B represents $—CH_2CH_2CH_2—$, and $R^1$ and $R^2$ each represents H, and $R^3$ represents 4-methylphenyl, and $L_1$ represents $—CH_2—$, then $R^4$ does not represent H or p-toluenesulfonyloxy;

and provided that if a fused ring is present, then the ring is fused to A;

or a pharmaceutically acceptable salt thereof.

2. A compound of claim 1 wherein:

A is selected from $—(CXY)_p—$; $—(CXY)_qCY{=}CY(CXY)_r—$; and

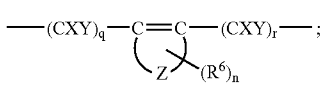

and B is $—(CXY)_p—$ or $—(CXY)_qCY{=}CY(CXY)_r—$;

where X is selected from H, halogen, $NO_2$, CN, $R^{12}$, $—OR^{11}$, $—SR^{11}$, $—SO_2R^{12}$, $—COR^{11}$, $—CO_2R^{11}$, $—CON(R^{11})_2$, $—OCOR^{12}$, $—N(R^{11})_2$ and $—NR^{11}COR^{12}$;

Y is H or $C_{1-6}$alkyl;

or X and Y together represent =O, =S, $=N—OR^{11}$ or $=CHR^{11}$;

with the proviso that neither A nor B comprises more than one —(CXY)— moiety that is other than $—CH_2—$;

Z completes an aryl or heteroaryl ring;

$R^6$ represents halogen, $NO_2$, CN, $R^{12}$, $—OR^{11}$, $—SR^{11}$, $—SO_2R^{12}$, $—COR^{11}$, $—CO_2R^{11}$, $—CON(R^{11})_2$, $—OCOR^{12}$, $—N(R^{11})_2$ and $—NR^{11}COR^{12}$;

n is 0, 1 or 2;

p is 2, 3 or 4; and q and r are independently 0 or 1.

3. A compound of claim 2 wherein:

X and Y are both H, or together represent =O, =NOH or $=CH_2$;

Z completes a benzene ring;

$R^6$ is halogen, CN, Ar, $—OR^{11}$ or $—N(R^{11})_2$;

n is 0 or 1; and q and r are both 1.

4. A compound of claim 2 of formula II:

II

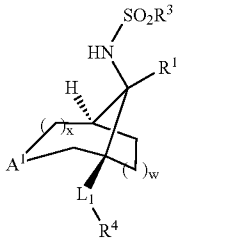

where $A^1$ represents $—CH_2—$, $—CH_2CH_2—$, —CH=CH— or

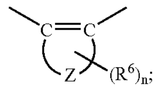

w is 1 or 2; and x is 0 or 1.

5. A compound of claim 1 wherein:

$R^3$ is selected from $C_{1-6}$alkyl which is optionally substituted with up to 3 halogen atoms, $C_{2-6}$alkenyl, phenyl optionally bearing up to 3 substituents selected from halogen, CN, $NO_2$ and $C_{1-6}$alkyl, and heteroaryl selected from pyridine, thiophene, thiazole and isothiazole, any of which heteroaryl groups optionally bearing up to 3 substituents selected from halogen, CN, $NO_2$ and $C_{1-6}$alkyl;

$R^4$ is selected from H, $OR^9$, $N(R^9)_2$, $CON(R^9)_2$, $OCN(R^9)_2$, CHO, CH=NOH, $CO_2R^9$, Ar, CN, Br, $OSO_2NH_2$ and heterocyclyl, where $R^9$ is H or $C_{1-6}$alkyl or two $R^9$ groups attached to the same nitrogen complete a heterocyclic ring;

and $L_1$ is selected from a covalent bond, $CH_2$, $CH_2CH_2$, CH=CH, $CH{=}CHCH_2$, $CH_2—W—CH_2$, $CH_2—W—CH_2CH_2$ and $CH_2—W—CH_2CH_2CH_2$.

6. A method of treating a subject suffering from or prone to Alzheimer's disease, which comprises administering to the subject an effective amount of a compound of formula I as defined in claim 1 or a pharmaceutically acceptable salt thereof.

7. A pharmaceutical composition comprising a compound of formula I:

I

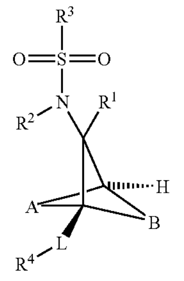

wherein:

A and B together with the carbon atoms bonded to $-L_1R^4$ and H complete a ring containing 5–10 carbon atoms, said ring bearing 0–2 substituents (in addition to $-L_1-R^4$) selected from:

=O, =S, $=N—OR^{11}$, $=CHR^{11}$, halogen, $NO_2$, CN, $R^{12}$, $—OR^{11}$, $—SR^{11}$, $—SO_2R^{12}$, $—COR^{11}$, $—CO_2R^{11}$, $—CON(R^{11})_2$, $—OCOR^{12}$, $—N(R^{11})_2$ and $—NR^{11}COR^{12}$;

and said ring optionally having fused thereto a further ring selected from $C_{6-10}$aryl, heteroaryl, heterocyclyl and $C_{5-10}$cycloalkyl, said further ring bearing 0–3 substituents independently selected from:

halogen, $NO_2$, CN, $R^{12}$, $—OR^{11}$, $—SR^{11}$, $—SO_2R^{12}$, $—COR^{11}$, $—CO_2R^{11}$, $—CON(R^{11})_2$, $—OCOR^{12}$, $—N(R^{11})_2$ and $—NR^{11}COR^{12}$;

$R^1$ represents H, $C_{1-4}$alkyl or $C_{2-4}$alkenyl;

$R^2$ represents H, or $C_{2-6}$acyl which optionally bears a carboxylic acid or amino substituent;

$R^3$ represents $C_{1-10}$alkyl, $C_{3-10}$cycloalkyl, $C_{2-6}$alkenyl, $C_{2-6}$alkynyl, $C_{6-10}$aryl$C_{1-6}$alkyl, heteroaryl$C_{1-6}$alkyl, $C_{6-10}$aryl$C_{2-6}$alkenyl, heteroaryl$C_{2-6}$alkenyl, $C_{6-10}$aryl, heteroaryl, or heterocyclyl; wherein the alkyl, cycloalkyl, alkenyl and alkynyl groups represented by $R^3$ or forming part of a group represented by $R^3$ optionally bear a substituent selected from halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$NR^7CO_2R^8$ and —$NR^7SO_2R^8$; and the aryl, heteroaryl and heterocyclic groups represented by $R^3$ or forming part of a group represented by $R^3$ optionally bear up to 3 substituents independently selected from $R^8$, halogen, CN, $NO_2$, —$OR^7$, —$SR^7$, —$S(O)_tR^8$ where t is 1 or 2, —$N(R^7)_2$, —$COR^7$, —$CO_2R^7$, —$OCOR^8$, —$CON(R^7)_2$, —$NR^7COR^8$, —$NR^7CO_2R^8$ and —$NR^7SO_2R^8$;

$R^4$ represents H, halogen, Ar, heterocyclyl, CN, —$OR^9$, —$N(R^9)_2$, —$N(R^9)COR^{10}$, —$N(R^9)CO_2R^{10}$, —$OCOR^{10}$, —$COR^9$, —$C(=NOR^{11})R^9$, —$CO_2R^9$, —$OCO_2R^{10}$, —$OSO_2R^9$, —$OSO_2N(R^9)_2$, —$CON(R^9)_2$, —$OCON(R^9)_2$, or —$CSN(R^9)_2$;

$L_1$ represents a covalent bond, $C_{1-6}$alkylene, $C_{2-6}$alkenylene, $C_{2-6}$alkynylene or $C_{1-4}$alkylene-W—$C_{1-4}$alkylene where W represents O, S, $SO_2$, NH, NH—CO—NH, O—CO—O, O—CO—NH or NH—CO—O, any of the alkylene groups optionally being substituted by halogen, CN, hydroxyl or $C_{1-4}$alkoxy; provided that if $R^4$ represents H, then $L_1$ does not represent a covalent bond;

$R^7$ represents H or $R^8$; or two $R^7$ groups together with a nitrogen atom to which they are mutually attached may complete a pyrrolidine, piperidine, piperazine or morpholine ring;

$R^8$ represents $C_{1-6}$alkyl, perfluoro$C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, Ar or —$C_{1-6}$alkylAr;

$R^9$ represents H or $R^{10}$; or two $R^9$ groups together with a nitrogen atom to which they are mutually attached may complete a 3–7 membered ring comprising up to 2 heteroatoms independently selected from N, O and S in addition to the nitrogen to which the $R^9$ groups are attached, said ring being optionally substituted by up to 3 substituents independently selected from halogen, oxo, $NO_2$, CN, $R^{12}$, —$OR^1$, —$SR^{11}$, —$SO_2R^{12}$, $COR^{11}$, —$CO_2R^{11}$, —$CON(R^{11})_2$, —$OCOR^{12}$, —$N(R^{11})_2$ and —$NR^{11}COR^{12}$;

$R^{10}$ represents $C_{1-6}$alkyl, perfluoro$C_{1-6}$alkyl, $C_{3-7}$cycloalkyl, $C_{3-6}$cycloalkyl$C_{1-6}$alkyl, $C_{2-6}$alkenyl, $C_{2-6}$alkynyl, $C_{6-10}$aryl, heteroaryl, heterocyclyl, $C_{6-10}$aryl$C_{1-6}$alkyl, heteroaryl$C_{1-6}$alkyl, $C_{6-10}$aryl$C_{2-6}$alkenyl or heteroaryl$C_{2-6}$alkenyl, wherein the alkyl, cycloalkyl, alkenyl and alkynyl groups optionally bear one substituent selected from halogen, $CF_3$, $NO_2$, CN, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$; and the aryl, heteroaryl and heterocyclic groups optionally bear up to 3 substituents independently selected from halogen, $NO_2$, CN, $R^{12}$, —$OR^{11}$, —$SR^{11}$, —$SO_2R^{12}$, —$COR^{11}$, —$CO_2R^{11}$, —$CON(R^{11})_2$, —$OCOR^{12}$, —$N(R^{11})_2$ and —$NR^{11}COR^{12}$;

$R^{11}$ represents H or $R^{12}$;

$R^{12}$ represents $C_{1-6}$alkyl, hydroxy$C_{1-6}$alkyl, perfluoro$C_{1-6}$alkyl, $C_{2-6}$alkenyl, $C_{2-6}$alkynyl, Ar or —$C_{1-6}$alkylAr;

Ar is phenyl or heteroaryl either of which optionally bears up to 3 substituents independently selected from halogen, OH, $CF_3$, $NO_2$, CN, $C_{1-6}$alkyl and $C_{1-6}$alkoxy;

heterocyclyl at every occurrence thereof means a cyclic or polycyclic system of up to 10 ring atoms selected from C, N, O and S, wherein none of the constituent rings is aromatic and wherein at least one ring atom is other than C; and heteroaryl at every occurrence thereof means a cyclic or polycyclic system of up to 10 ring atoms selected from C, N, O and S, wherein at least one of the constituent rings is aromatic and wherein at least one ring atom of said aromatic ring is other than C;

and provided that if a fused ring is present, then the ring is fused to A;

or a pharmaceutically acceptable salt thereof;

and a pharmaceutically acceptable carrier.

8. A method of treating a subject suffering from or prone to Alzheimer's disease which comprises administering to the subject a pharmaceutically composition of claim 7.

* * * * *